US008877183B2

(12) United States Patent
Foster et al.

(10) Patent No.: US 8,877,183 B2
(45) Date of Patent: *Nov. 4, 2014

(54) METHODS FOR TREATMENT OF OCULAR DISEASES

(71) Applicant: Board of Supervisors of Louisiana State University and Agricultural and Mechanical College, Baton Rouge, LA (US)

(72) Inventors: Timothy Paul Foster, Slidell, LA (US); Paulo Cesar Rodriguez, Metarie, LA (US); James Milton Hill, New Orleans, LA (US); Augusto Ochoa, New Orleans, LA (US)

(73) Assignees: National Institutes of Health (NIH), Washington, DC (US); U.S. Dept. of Health and Human Services (DHHS), Washington, DC (US); NIH Division of Extramural Inventions and Technology Resources (DEITR), Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/828,669

(22) Filed: Mar. 14, 2013

(65) Prior Publication Data

US 2013/0344049 A1   Dec. 26, 2013

Related U.S. Application Data

(60) Provisional application No. 61/664,464, filed on Jun. 26, 2012.

(51) Int. Cl.
| A61K 38/46 | (2006.01) |
| A61K 38/54 | (2006.01) |
| A61K 47/48 | (2006.01) |
| A61K 38/50 | (2006.01) |

(52) U.S. Cl.
CPC ......... *A61K 38/50* (2013.01); *C12Y 305/03001* (2013.01); *A61K 47/48215* (2013.01)
USPC ...................................... 424/94.6; 424/94.3

(58) Field of Classification Search
USPC ............................... 424/94.3, 94.6
See application file for complete search history.

(56) References Cited

U.S. PATENT DOCUMENTS

| 4,409,205 | A | * | 10/1983 | Shively ................. 424/78.04 |
| 5,766,897 | A | | 6/1998 | Braxton |
| 7,973,079 | B2 | | 7/2011 | Mata et al. |
| 2002/0110553 | A1 | | 8/2002 | Fleiszig et al. |
| 2005/0192210 | A1 | | 9/2005 | Rothbard et al. |
| 2006/0167088 | A1 | | 7/2006 | Widder et al. |
| 2009/0118243 | A1 | | 5/2009 | Gjorstrup |
| 2010/0247508 | A1 | | 9/2010 | Leung et al. |

FOREIGN PATENT DOCUMENTS

| KR | WO0209741 A1 | 2/2002 |
| WO | WO2010051533 A2 | 5/2010 |
| WO | WO2011008495 A2 | 1/2011 |

OTHER PUBLICATIONS

Kang et al. Emerging Pegylated Drugs; Expert Opinion: Emerging Drugs, vol. 14, No. 2 (2009) pp. 363-380.*
Kahan et al. The Significance of the Arginine and Arginase of Tears in Experimentally-Induced Herpes Simplex Corneae; Albrecht v. Graefes Arch. klin. exp. Ophthal, vol. 209 (1979) pp. 219-224.*
Serhan et al. Resolution of Inflammation: State of the Art, Definitions and Terms; Faseb Journal, vol. 21, No. 2 (2007) pp. 325-332.*
Chirife et al. In Vitro Antibacterial Activity of Concentrated Polyethylene Glycol 400 Solutions; Antimicrobial Agents and Chemotherapy, vol. 24, No. 3 (1983) pp. 409-412.*
Pasut G et al, PEG conjugates in clinical development or use as anticancer agents: An overview, Advanced Drug Delivery Review, vol. 61, No. 13, Nov. 12, 2009.
Caldwell R B et al, Vascular dysfunction in retinopathy an emerging role for arginase, Brain Research Bulletin, vol. 81, No. 2-3, Feb. 15, 2010.

* cited by examiner

*Primary Examiner* — Susan Hanley
*Assistant Examiner* — Paul Martin
(74) *Attorney, Agent, or Firm* — Jason P. Mueller; Adams and Reese

(57) ABSTRACT

Methods and therapeutic treatments of ocular diseases are provided including applying peg-Arginase I to affected eyes. Methods are provided that simultaneously treat inflammation and neovascularization of eyes while promoting healing. Methods are provided to treat lesions or infections of an eye.

24 Claims, 33 Drawing Sheets peg-ArgI Treatment Inhibits Cell-to-Cell Transmission and Spread of HSV peg-ArgI is effective at inhibiting viral replication of acyclovir resistant herpesviruses peg-ArgI is effective at inhibiting viral replication of acyclovir resistant herpesviruses

Representative Eyes from Ocular HSV-1 Treatment Studies peg-ArgI Prevents Adenovirus-mediated Cellular Cytopathic Effects

Adenovirus Type 5
MOI=200

Assessment of Treatments on VEGF-Mediated Vascular Endothelial Cell Migration

Representative Images of Treatment Effects on VEGF-mediated Corneal Neovascularization

METHODS FOR TREATMENT OF OCULAR DISEASES

CROSS-REFERENCE TO RELATED APPLICATIONS

This application claims benefit of U.S. Provisional Application 61/664,464 filed Jun. 26, 2012, which is incorporated herein by reference.

STATEMENT REGARDING FEDERALLY SPONSORED RESEARCH OR DEVELOPMENT

This invention was made with government support under grants P20RR021970 and P20GM103501 awarded by the National Institutes of Health. The government has certain rights in the invention.

FIELD

The present disclosure relates generally to treatment of ocular diseases. More particularly, the present disclosure relates to therapeutic methods to treat pathogen, trauma, and inflammation-mediated ocular diseases, including associated sequelae.

BACKGROUND

The cornea is the highly transparent outer-most layer of the eye that provides a large portion of the eye's refractive power and shields against infection by pathogens. Since even the smallest of cells can affect visual acuity, normal corneal tissue lacks all vasculature and is immunologically privileged to reduce influx of inflammatory cells. Generally, in the absence of ocular disease and/or trauma, the lack of vasculature and inflammatory response of the cornea ensures visual acuity is maintained. However, under certain ocular situations, the lack of vascularization and/or suppressed inflammatory response may be compromised.

For example, trauma to the eye by a foreign object (e.g. dust, sand, or mechanical), a surgical procedure (e.g. refractive surgery or transplantation), or infection of the cornea with viruses, bacteria, or other infectious agents, may initiate an inflammatory reaction mediated by the immune response and neovascularization (formation of new blood vessels). These processes may result in destructive cytopathic causes and may lead to thickening and opacification (clouding) of the cornea, which may ultimately lead to a reduction of visual clarity and sometimes sight.

Trauma of the cornea (e.g., surgical or accidental) may lead to pain, inflammation, scarring, neovascularization, and/or discharge. Even in the absence of a particular infectious agent, corneal lesions can affect visual acuity and progress to further damage to the eye. Generally, corneal trauma may be typically treated with strong corticosteroids which may decrease inflammation. However, these agents may have severe secondary effects, including: 1) increased risk of infections (common in ocular trauma) by diminishing the protective immune response; 2) delayed healing of the cornea; 3) loss of an intact epithelial barrier; 4) increased ocular pressure; and 5) eventual deterioration of vision.

Globally, infection- and inflammation-associated eye diseases are the leading causes of corneal blindness and visual morbidity, with over 500 million individuals affected. Pathogen-associated ocular diseases are a complex combination of pathogen-mediated trauma and host-mediated pathologies, often with the most severe sequelae being a consequence of host inflammatory responses. Corneal infections are often treated with a combination of antimicrobials to eliminate pathogens and corticosteroids to reduce inflammation. However, several problems may arise from this approach.

First, effective antimicrobials are not always available for the infectious agents of the eye. For example, Adenoviral infections, which may cause epidemic outbreaks of highly contagious keratoconjunctivitis (pink eye) that can last up to a month, are not readily treatable by antimicrobials. Second, even when anti-viral medications are available and can kill the viruses, they cannot control the inflammatory response triggered by the infection. Typically, inflammation accounts for the clinical presentation of an ocular disease. Often the inflammatory response may cause secondary but more severe damage of the cornea. Third, many pathogens evolve drug resistance, which enables the pathogen to replicate even in the presence of the antimicrobial. For example, some strains of herpes simplex viruses (HSV), which are the leading cause of infectious corneal blindness in the United States, and *Chlamydia trachomatis*, a leading cause of infectious blindness worldwide, have developed drug resistant strains. Fourth, co-administration of steroids to suppress host anti-pathogen immune responses (inflammation) in infected individuals also blocks the protective role of the immune responses and enables uncontrolled replication, as well as pathogen-mediated disease progression.

Four herpes viruses are linked to severe infections of the eye that can result in blindness: HSV-1, HSV-2, VZV, and CMV. The National Eye Institute estimates that 450,000 Americans have experienced some form of ocular herpetic disease, with 50,000 new and recurrent cases diagnosed annually. Despite effective antivirals against HSV, approximately 25% of these cases develop serious inflammation-associated stromal keratitis. Individuals that have experienced ocular herpes have a 50% chance of recurrence with each repeated episode triggering deleterious CD4 and CD8 T cell responses that can result in scarring of the cornea and an eventual need for corneal transplantation. Although corneal transplantation restores the patient's sight, it does not cure the patient of his or her lifelong herpetic infection; therefore, recrudescence of infection in these individuals may renew the vicious cycle and result in damage to the implanted cornea.

Herpetic stromal keratitis (HSK), a blinding eye disease associated with HSV-1 infection, is not simply a virus-mediated disease of the corneal stroma, but a virus-associated chronic immuno-inflammatory disease of the eye. It is mediated by many complex immune mechanisms including macrophages, dendritic cells, T cells (Th1, Th2, T-regs and Th17), antibodies and even cytokines. Therefore, even with anti-herpetic drugs controlling HSV-1 replication, the vision threatening disease progresses through immune-mediated pathologies.

Clinical presentations of ocular diseases are a complex combination of trauma and host-mediated inflammation-associated pathologies that must be simultaneously controlled and resolved to prevent development of vision-threatening sequelae. Currently, no treatments exist that can effectively remedy all of these issues within the eye. Accordingly, there is need for an innovative approach to treat trauma, pathogen, and inflammation-associated ocular diseases.

SUMMARY

In an embodiment of the present invention, a method of simultaneously inhibiting inflammation and neovascularization of corneal tissue of an eye and promoting healing of the eye is provided, including applying peg-Arginase I to the eye.

The peg-Arginase I is applied exogenously. The eye may have been infected with an infectious agent. The infectious agent may be a virus. The peg-Arginase I may inhibit replication of the virus. The infectious agent may be a bacteria.

The eye may have been traumatized. The trauma may be from a medical procedure. The trauma may be from an accidental injury of the eye.

The peg-Arginase I may part of an ophthalmic formulation. The ophthalmic formulation may include peg-Arginase I and free peg molecules. The ophthalmic formulation may further include pH buffers. The ophthalmic formulation may be an eye drop. The eye may be a mammalian eye. The mammalian eye may be a human eye.

According to an embodiment of the present invention, a therapeutic method to treat an ocular disease is provided, including applying peg-Arginase I to an affected eye. The peg-Arginase I is part of an ophthalmic formulation. The affected eye may present at least one of inflammation and neovascularization. The ocular disease may be caused by an infectious agent. The infectious agent may be a virus. The peg-Arginase I may inhibit replication of the virus. The infectious agent may be a bacteria.

The ocular disease may be trauma to the affected eye. The trauma may be from a medical procedure. The ocular disease may be a corneal lesion.

According to an embodiment of the present invention, an ocular anti-viral treatment is provided, including applying peg-Arginase I to an infected eye. The peg-Arginase I is part of an ophthalmic formulation. Replication of the pathogen may be inhibited. The eye may be infected by at least one of HSV-1, HSV-2, CMV, VZV and Adenovirus. The at least one of HSV-1, HSV-2, CMV, VZV and Adenovirus may be drug resistant.

According to an exemplary embodiment of the present invention, a method to promote healing of corneal trauma is provided, including applying peg-Arginase I to an affected eye. The trauma may be induced by at least one of accidental injury, surgical procedure, mechanical impact, and pathogenic infection.

According to an exemplary embodiment of the present invention, a method to treat ocular lesions is provided including applying peg-Arginase I to an affected eye. The peg-Arginase I is part of an ophthalmic formulation. The ophthalmic formulation may be comprised of peg-Arginase I and free peg molecules.

According to an exemplary embodiment of the present invention, a method to prevent ocular neovascularization is provided, including applying peg-Arginase I to an affected eye. The peg-Arginase I is part of an ophthalmic formulation. The ophthalmic formulation may be comprised of peg-Arginase I and free peg molecules.

According to an exemplary embodiment of the present invention, a method to prevent ocular inflammation is provided, including applying peg-Arginase I to an affected eye. The peg-Arginase I is part of an ophthalmic formulation. The ophthalmic formulation may be comprised of peg-Arginase I and free peg molecules.

DESCRIPTION

Figure 1A:
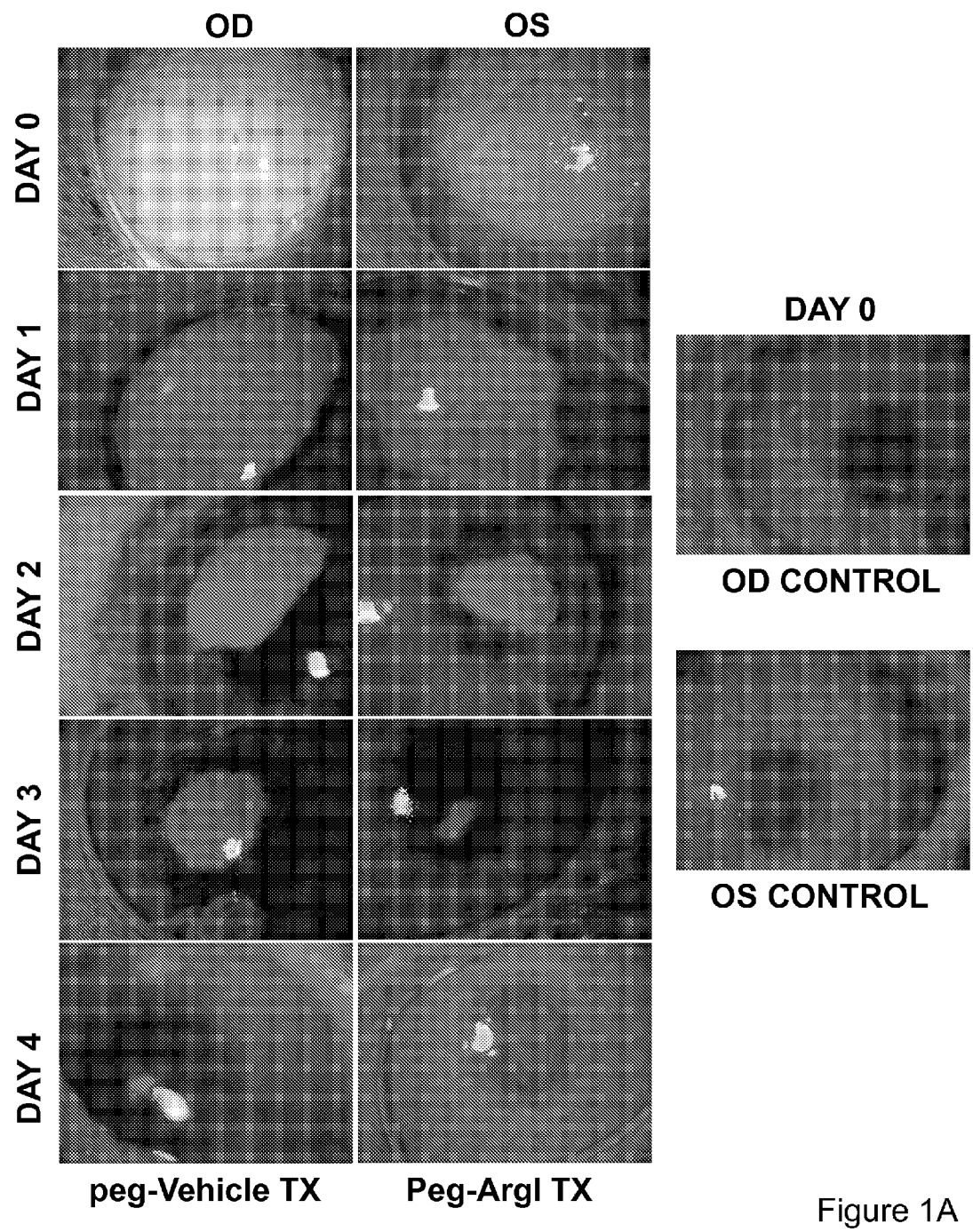
FIG. 1A is a series of images of rabbit eyes with an 8 mm (area=200 mm$^2$) region of cornea surgically debrided and treated with peg vehicle or peg-Arginase I, according to an example embodiment of the present invention.

Embodiments of the present disclosure provide a formulation of pegylated arginase I (peg-Arginase I) that simultaneously treats inflammatory reactions and neovascularization of corneal tissue, while promoting healing of a damaged cornea. Embodiments may include peg-Arginase I as part of an ophthalmic formulation, which may be applied topically to an affected eye. Embodiments of the present disclosure provide methods for improved treatment of ocular diseases whereby the methods simultaneously: (1) inhibit damaging inflammatory reactions without blocking protective host responses; (2) inhibit replication of multiple pathogens; (3) prevent neovascularization processes; and (4) promote healing. Further, embodiments of the present disclosure target pathways that are unlikely to lead to the evolution of drug resistance and may be effective against current drug resistant pathogens.

Arginase is a manganese-containing enzyme and is part of the urea cycle. In most mammals, two isozymes of arginase exist: (1) arginase I, which functions in the urea cycle and is located primarily in the cytoplasm of the liver, and (2) arginase II, which may regulate arginine/ornithine concentrations in the cell. Pegylation is the process of covalent attachment of polyethylene glycol (peg) polymer chains to another molecule such as a drug or protein. Pegylation may mask an agent from a host's immune system and may provide increased solubility, mobility and longevity to the agent. peg-Arginase I is a formulation of arginase I that has been pegylated.

In embodiments of the present invention, application of peg-Arginase I may occur exogenously and may be delivered as a topical ophthalmic formulation such as an eye drop. This peg-Arginase I ophthalmic eye drop may be composed of both protein conjugated and free PEG molecules which may facilitate enzyme stability and mask the peg-Arginase I from host responses. Presence of free PEG molecules may also impart properties to the formulation that aid in peg-Arginase I's ophthalmic activities. The peg-Arginase I eye drop may contain various buffer systems that maintain a pH level that is conducive for Arginase enzymatic activity and is tolerated by the eye. In certain embodiments, peg-Arginase I may be applied in combination with other antivirals, anti-inflammatories or anti-inflammatory treatments. peg-Arginase I application is effective in treating corneal trauma, promoting healing of the cornea, and preventing deleterious vision-threatening inflammation. It is also affective against both RNA and DNA viral infections, including both enveloped and non-enveloped viruses. Embodiments of the present invention may also be used to treat certain bacterial infections, including *Chlamydia trachomatis*. The present disclosure may be utilized to treat a variety of pathogen and inflammation-associated ocular diseases, including: Adenovirus-associated epidemic keratoconjunctivitis (no current effective treatment); herpes simplex-associated eye infections; varicella zoster-associated eye infections; herpes stromal keratitis; inflammation-associated diseases; CMV retinitis; and drug resistant pathogens. Moreover, embodiments may be used to treat humans or in various veterinarian applications, including feline, canine, and equine ocular diseases. The foregoing list is exemplary only and is not intended to identify all ocular diseases that may be treated with the methods identified herein.

Figure 1B:
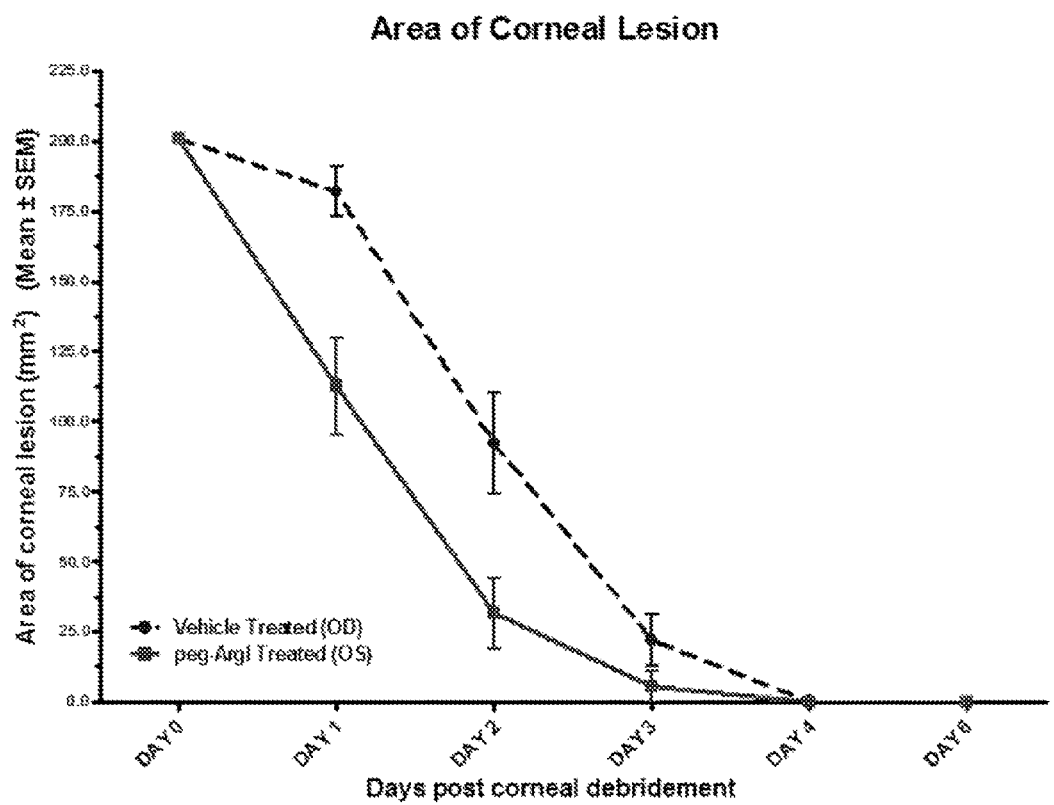
FIG. 1B is a line graph showing areas of the corneal lesions over a period of six days, as represented by eyes in FIG. 1A.

In an exemplary embodiment, the present disclosure may be employed to treat ocular lesions, which may be caused by accidental or surgical trauma. Application of peg-Arginase I to a corneal lesion accelerates wound healing while reducing or eliminating ocular inflammation, neovascularization and inflammatory discharge. FIGS. 1 through 4 and Tables 1 through 5 demonstrate experimental results of an embodiment of the present disclosure whereby surgically—induced corneal lesions were treated with peg-Arginase I. FIG. 1A shows representative images of the lesions and demonstrates that treatment with an embodiment of the present invention accelerated healing of the lesion compared to peg-vehicle treatments. As shown in FIG. 1B and Tables 1 and 2, rates of corneal healing and injury closure were substantially faster when treated with an embodiment of the present invention, with 100% of eyes reaching clinical cure for epithelial defects two days faster than those treated only with peg-vehicle.

TABLE 1

Calculated Times of Corneal Epithelium Closure

| % Closure | peg-ArgI | Vehicle |
| --- | --- | --- |
| 25% | 14 h | 36 h |
| 50% | 30 h | 48 h |
| 75% | 38 h | 64 h |

TABLE 2

Number of Eyes Clinically Cured for Area of Corneal Debridement

| DAY | Number Eyes Clinically Cured (peg-ArgI) | Number Eyes Clinically Cured (Vehicle) |
| --- | --- | --- |
| 0 | 0/5 | 0/5 |
| 1 | 0/5 | 0/5 |
| 2 | 0/5 | 0/5 |
| 3 | 3/5 (60%) | 1/5 (20%) |
| 4 | 5/5 (100%) | 2/5 (40%) |
| 6 | 5/5 (100%) | 5/5 (100%) |

Figure 2:
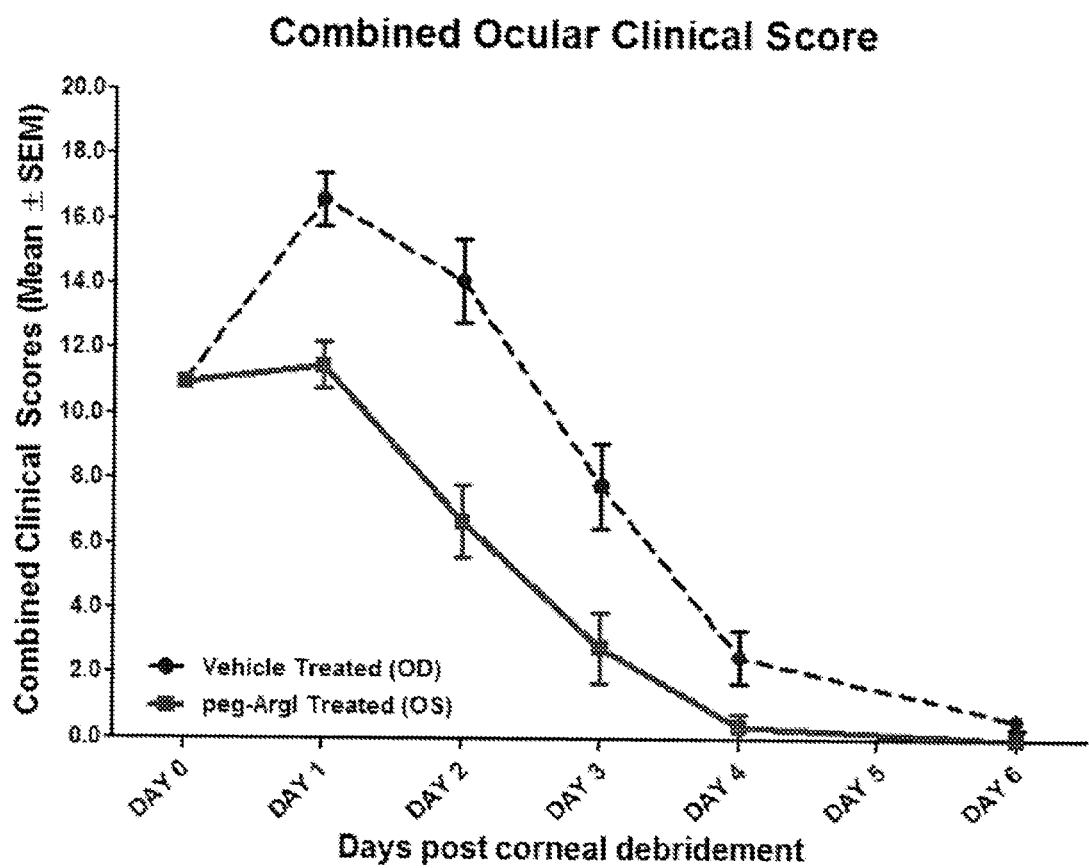
FIG. 2 is a line graph showing combined ocular clinical scores over a period of six days, as represented by eyes in FIG. 1A.

Moreover, as shown in FIG. 2 and Table 3, peg-Arginase I treated eyes did not experience an increase in presentation of any clinical symptoms, and combined clinical presentations markedly declined with treatment. On day four, 80% of eyes treated with an embodiment of the present invention exhibited no symptomology from the surgically-induced trauma with all eyes clinically cured by day six. In contrast, only 40% of vehicle treated eyes showed clinical cure for all ocular parameters by day six of treatment.

TABLE 3

Number of Eyes Clinically Cured of All Combined Ocular Clinical Conditions

| DAY | Number Eyes Clinically Cured (peg-ArgI) | Number Eyes Clinically Cured (Vehicle) |
| --- | --- | --- |
| 0 | 0/5 | 0/5 |
| 1 | 0/5 | 0/5 |
| 2 | 0/5 | 0/5 |
| 3 | 0/5 | 0/5 |
| 4 | 4/5 (80%) | 0/5 |
| 6 | 5/5 (100%) | 2/5 (40%) |

Figure 3:
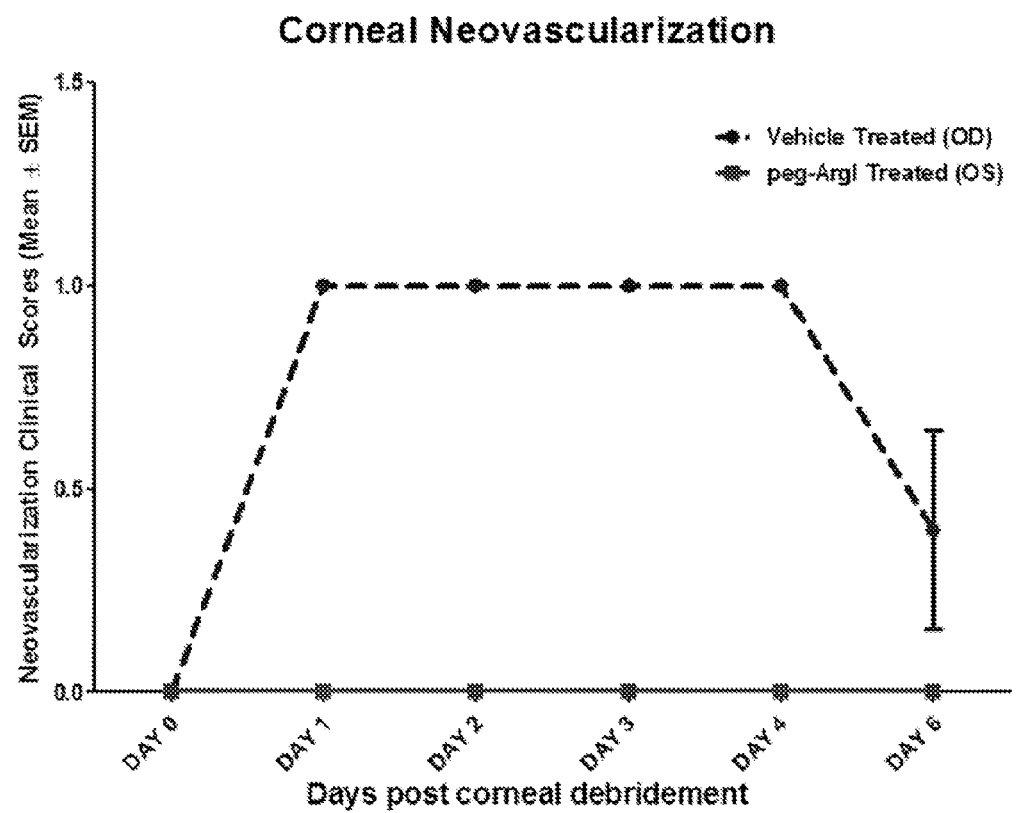
FIG. 3 is a line graph showing corneal neovascularization over a period of six days, as represented by eyes in FIG. 1A.
Figure 4:
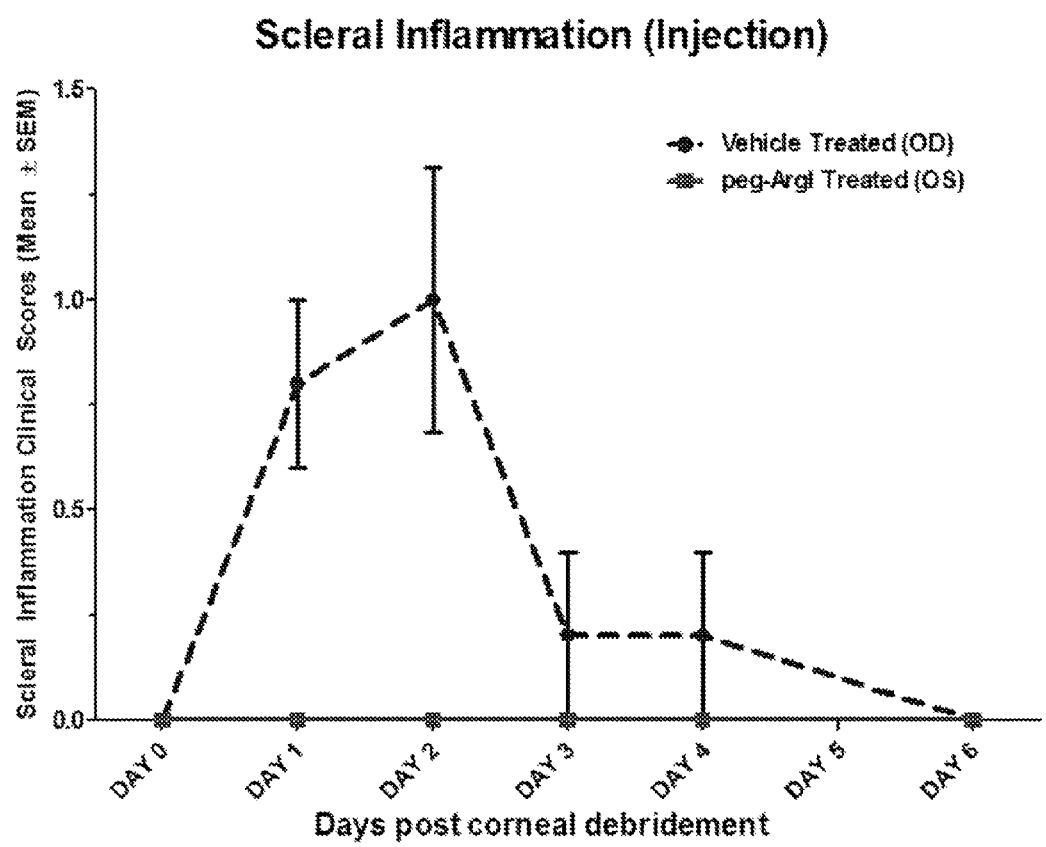
FIG. 4 is a line graph showing scleral inflammation over a period of six days, as represented by eyes in FIG. 1A.

FIGS. 3 and 4, as well as Tables 4 and 5, illustrate that treatment with an embodiment of the present invention prevents corneal neovascularization and inflammation of the sclera in this corneal wound healing model. These results not only demonstrate effectiveness of the present invention for treating traumatic ocular issues, but exemplify that embodiments of the ophthalmic formulation are well-tolerated in the eye even in the presence of traumatic damage.

TABLE 4

Number of Eyes Clinically Cured of Corneal Neovascularization

| DAY | Number Eyes Clinically Cured (peg-ArgI) | Number Eyes Clinically Cured (Vehicle) |
| --- | --- | --- |
| 0 | 5/5 (100%) | 5/5 (100%) |
| 1 | 5/5 (100%) | 0/5 |
| 2 | 5/5 (100%) | 0/5 |
| 3 | 5/5 (100%) | 0/5 |
| 4 | 5/5 (100%) | 0/5 |
| 6 | 5/5 (100%) | 3/5 (60%) |

TABLE 5

Number of Eyes Clinically Cured of Scleral Inflammation (Injection)

| DAY | Number Eyes Clinically Cured (peg-ArgI) | Number Eyes Clinically Cured (Vehicle) |
| --- | --- | --- |
| 0 | 5/5 (100%) | 5/5 (100%) |
| 1 | 5/5 (100%) | 1/5 (20%) |
| 2 | 5/5 (100%) | 1/5 (20%) |
| 3 | 5/5 (100%) | 4/5 (80%) |
| 4 | 5/5 (100%) | 4/5 (80%) |
| 6 | 5/5 (100%) | 5/5 (100%) |

Accordingly, embodiments of the present invention are effective in the treatment of ocular trauma, including reducing or eliminating inflammation, neovascularization and/or inflammatory discharge. Embodiments may substantially accelerate healing of the eye after an ocular trauma incident.

Figure 5:
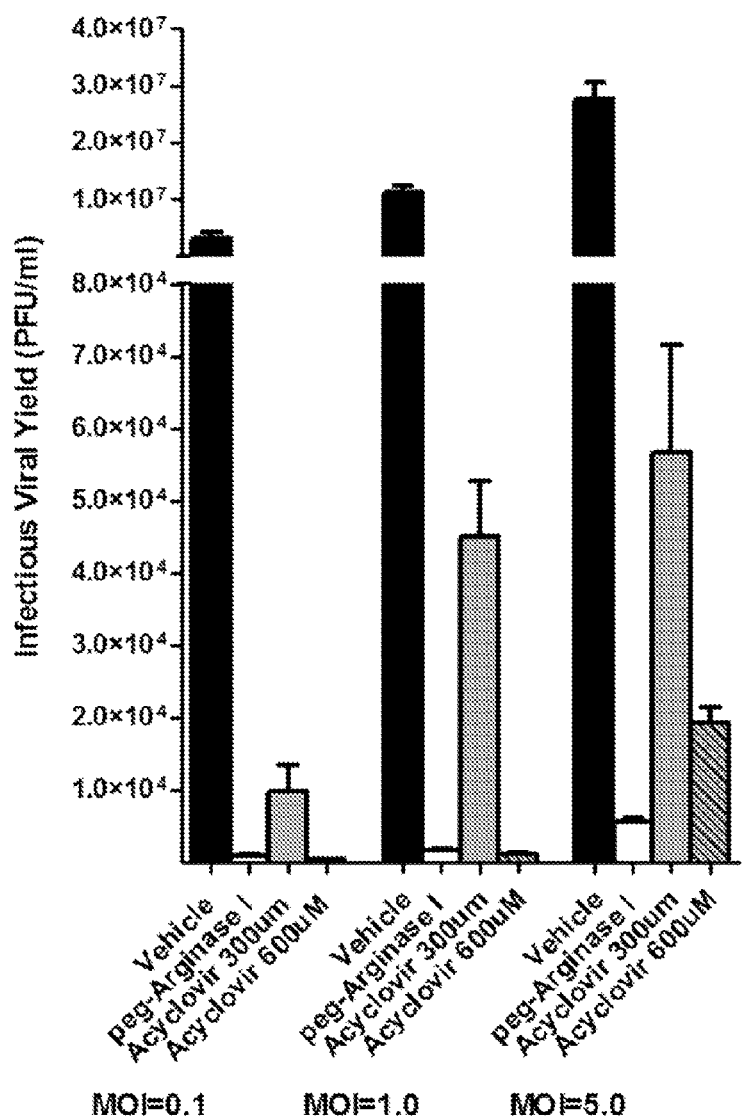
FIG. 5 is a bar graph showing infectious viral yield for cell cultures infected with HSV-1 and treated with a vehicle (peg vehicle), peg-Arginase I, or different concentrations of acyclovir, according to an example embodiment of the present invention.
Figure 6:
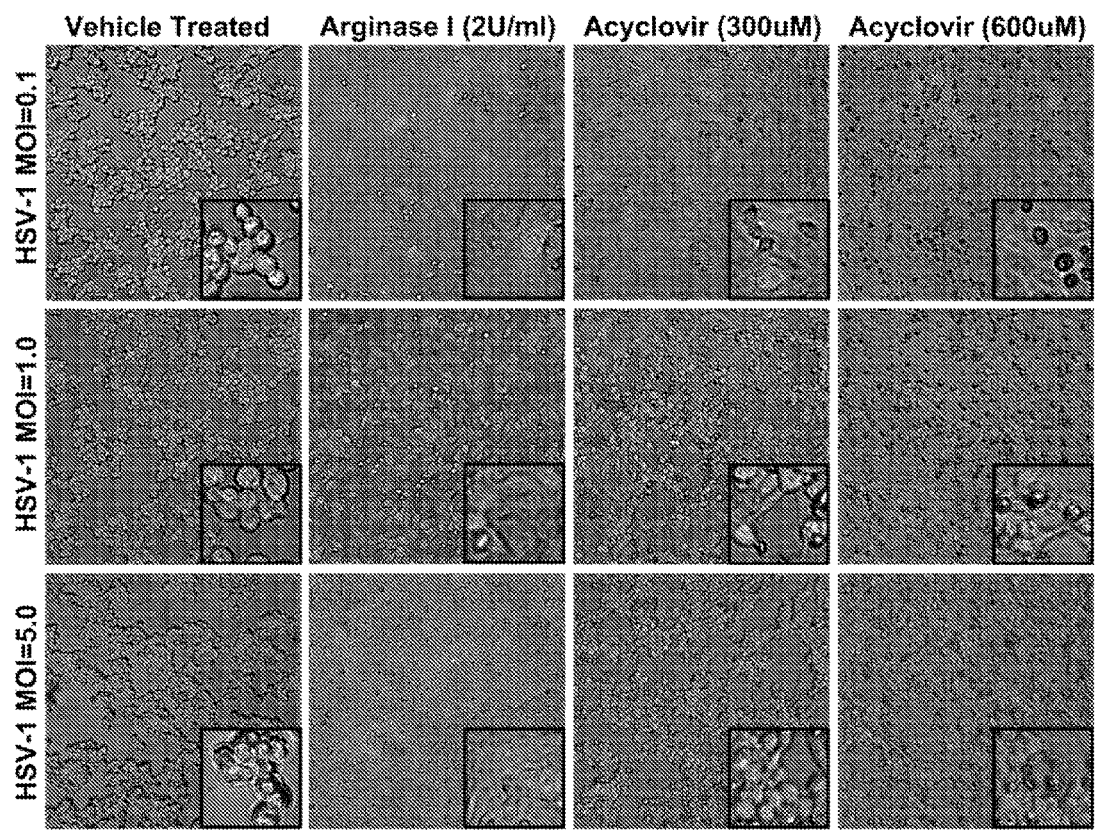
FIG. 6 is a series of images showing virus-mediated cytopathic effects on cell cultures treated as described in FIG. 5.
Figure 7A:
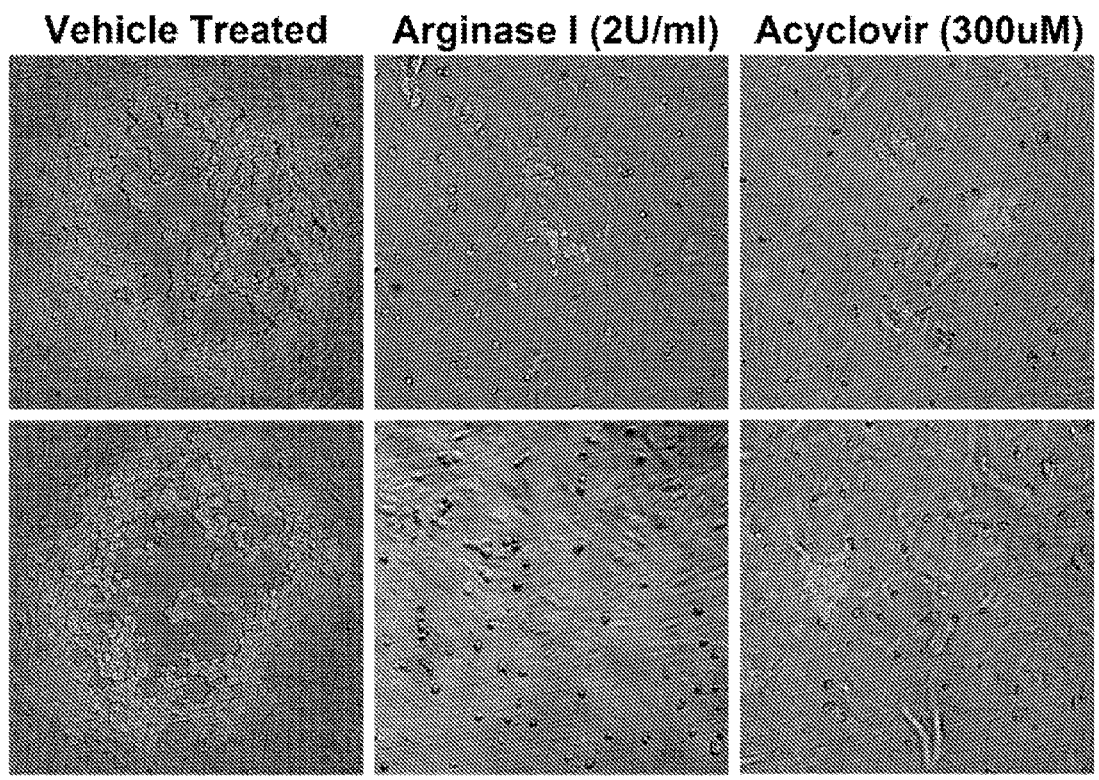
FIG. 7A is a series of images of HSV-plaques showing capacity for cell-to-cell spread following treatment with a vehicle (peg vehicle), peg-Arginase I, or acyclovir, according to an example embodiment of the present invention.
Figure 7B:
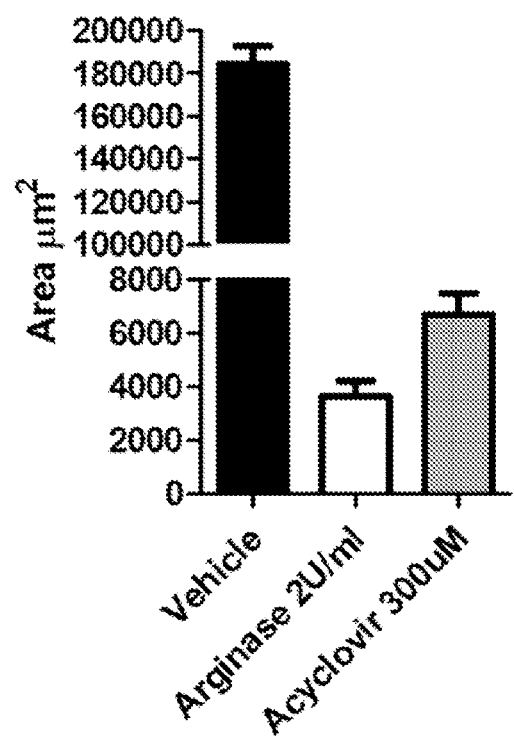
FIG. 7B is a bar graph showing effects of treatment on cell-to-cell spread of HSV-1 for cultures treated as described in FIG. 7A.
Figure 8A:
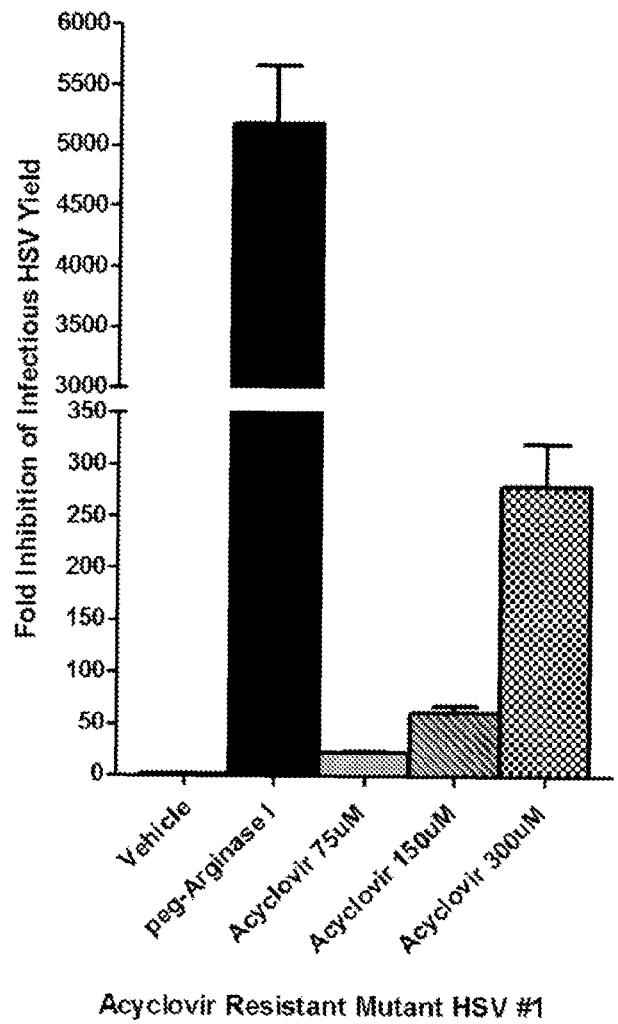
FIG. 8A is a bar graph showing infectious HSV yield for cell cultures infected with an acyclovir resistant mutant HSV, according to an example embodiment of the present invention.
Figure 8B:
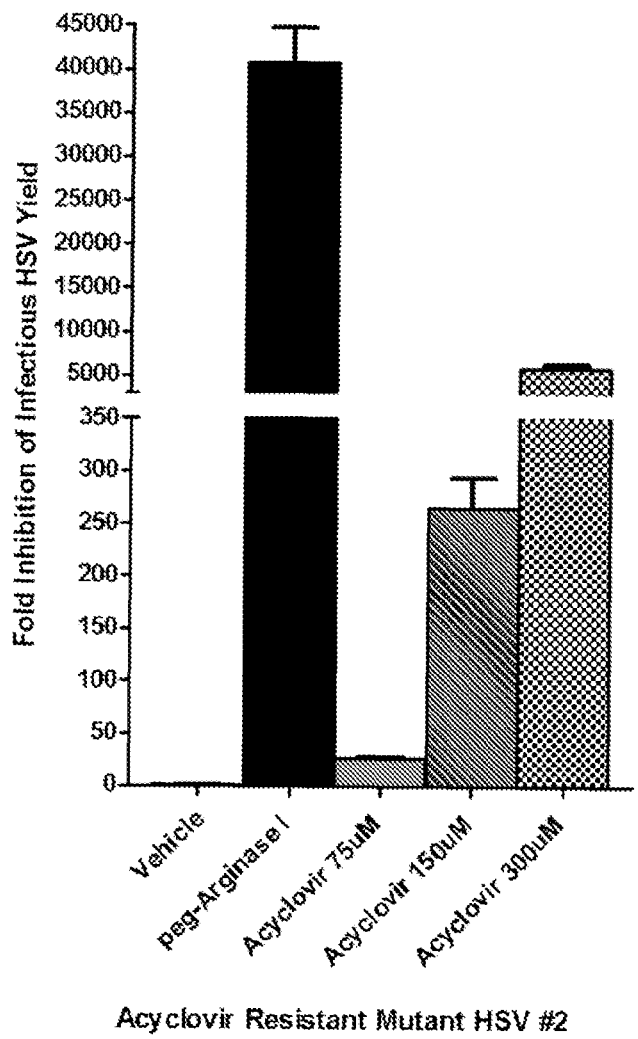
FIG. 8B is a bar graph showing infectious HSV yield for cell cultures infected with a different acyclovir resistant mutant HSV, according to an example embodiment of the present invention.
Figure 9:
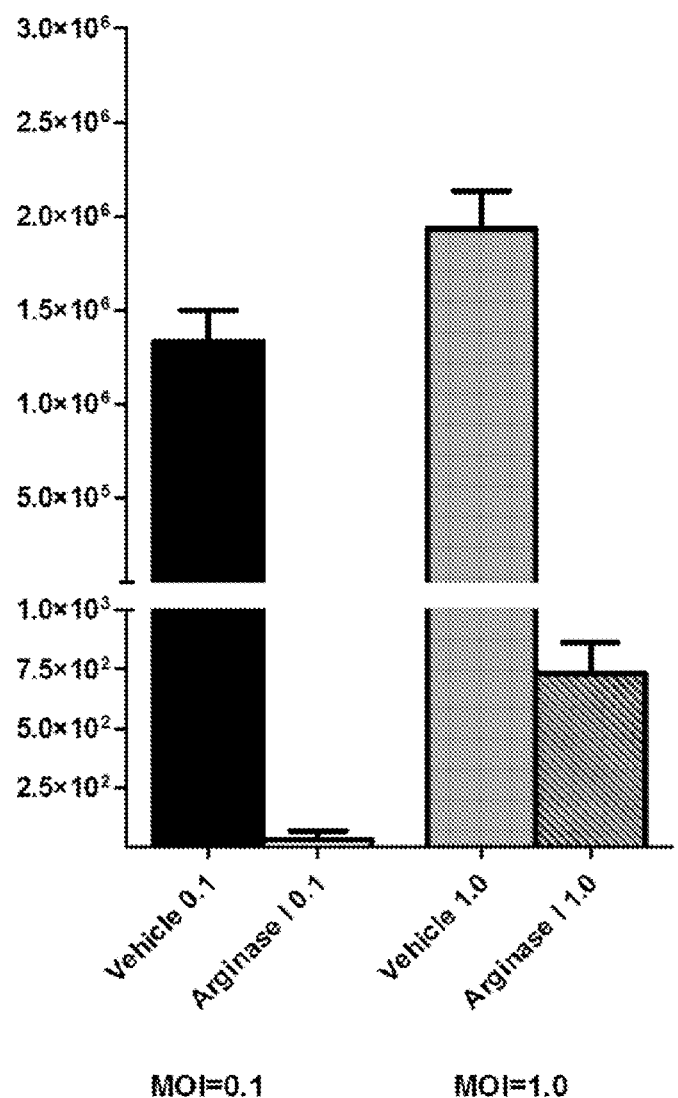
FIG. 9 is a bar graph showing replication of HSV-1 in primary corneal epithelial cell cultures treated with vehicle or peg-Arginase I, according to an example embodiment of the present invention.

In another exemplary embodiment, the present disclosure may be employed to treat pathogenic infections of the eye (e.g., herpes simplex virus types 1 and 2 (HSV-1 and HSV-2) and Adenovirus infections). Embodiments may be used as a treatment against wild-type and/or drug resistant herpes simplex virus (HSV) replication and/or transmission, as well as HSV-mediated inflammation-associated ocular disease. In FIG. 5, cells infected by HSV-1 and treated with an embodiment of the present invention inhibited production of infectious virus by greater than 1000 fold even at high multiplicities of infection (MOIs). The present invention was at least as effective as high doses of a common anti-herpetic, acyclovir. As shown in FIGS. 6 and 7, peg-Arginase I treatment blocked virus-associated cytopathic effects, viral transmission to uninfected cells, and cell-to-cell spread. FIGS. 8A and 8B demonstrate that, for two different drug resistant mutant HSV viruses, peg-Arginase I is highly efficient at inhibiting drug-resistant viral replication, while anti-herpetic drugs, such as acyclovir, are not functional against such strains, even at high doses. FIG. 9 illustrates that antiviral effects of peg-Arginase I were also observed in primary human corneal epithelial cells, a cell line that recapitulates the natural cells where herpesviruses replicate within the eye.

Figure 10:
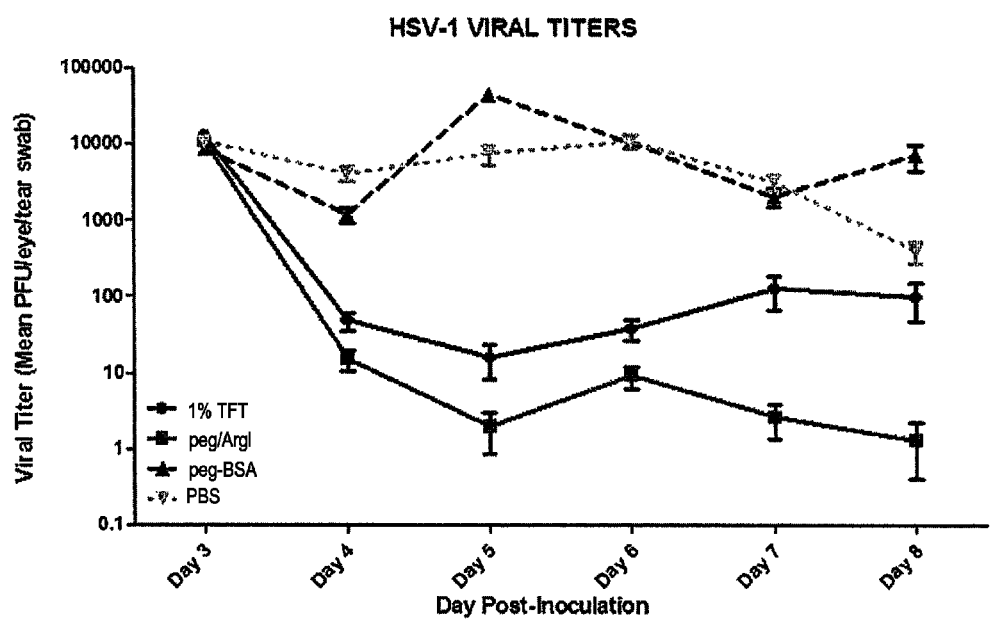
FIG. 10 is line graph showing viral production in a rabbit eye model for eyes infected with HSV-1 and treated with controls (peg-BSA and PBS), 1% triflourothymidine, or peg-Arginase I, according to an example embodiment of the present invention.
Figure 11:
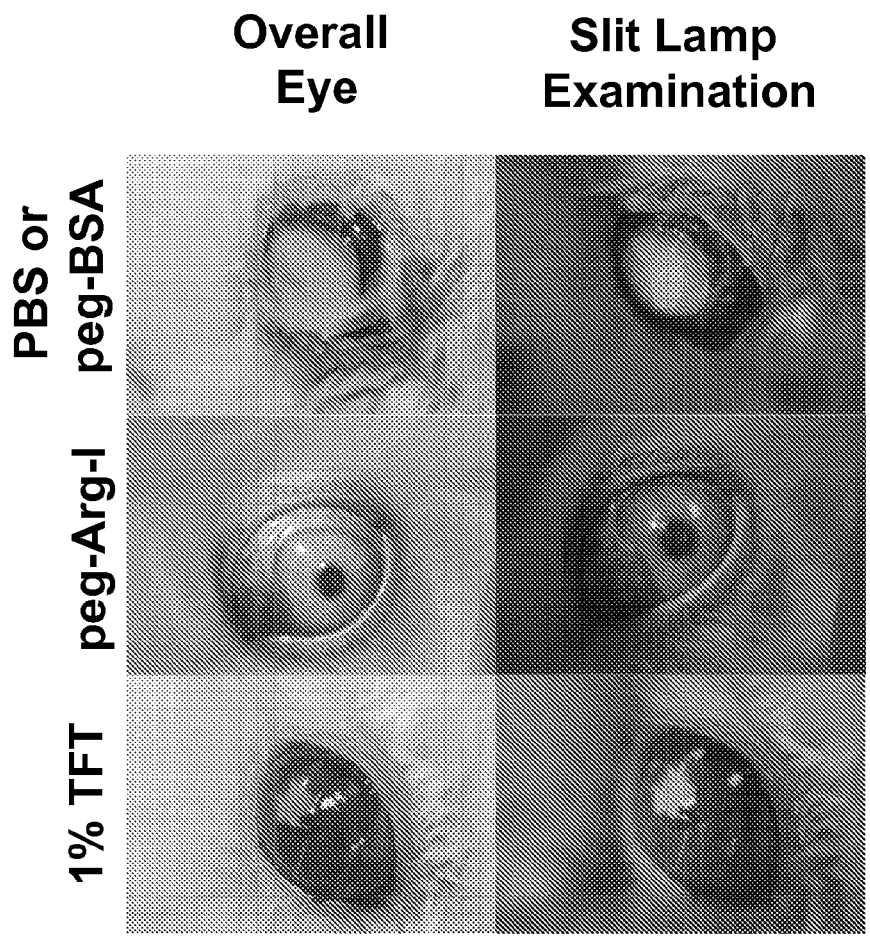
FIG. 11 is a series of images of rabbit eyes infected with HSV-1 and treated with controls (peg-BSA or PBS), 1% triflourothymidine, or peg-Arginase I, according to an example embodiment of the present invention.
Figure 12:
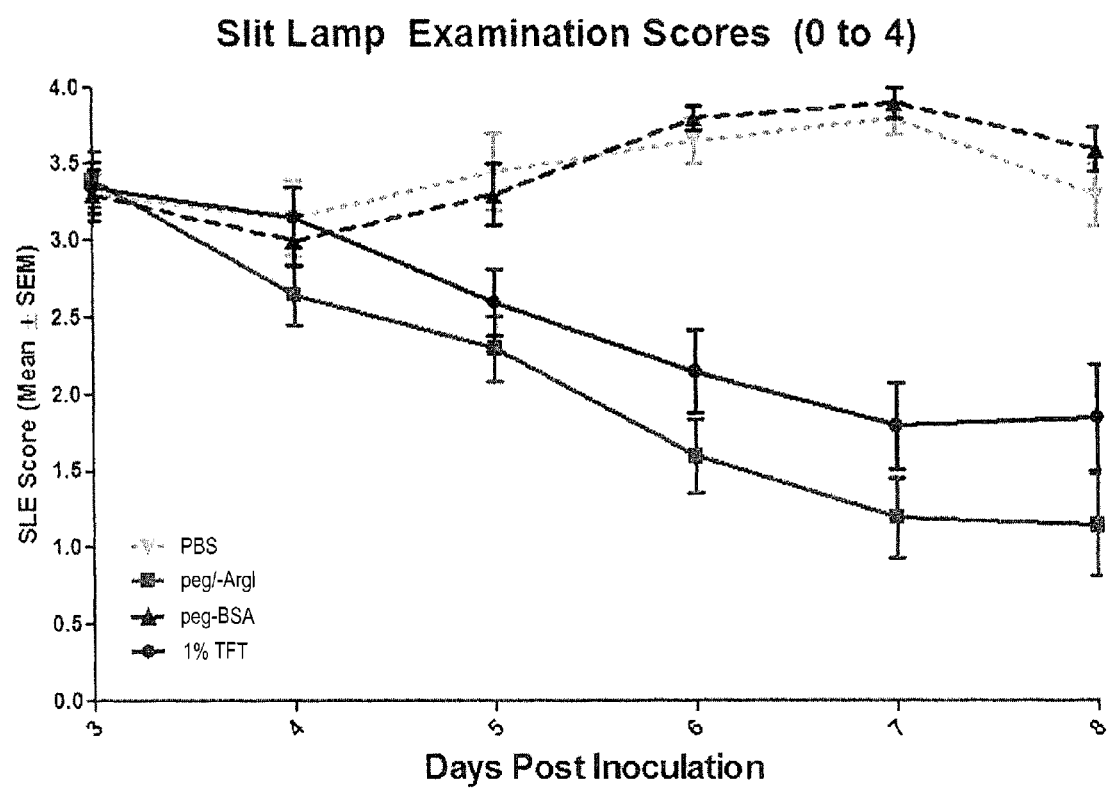
FIG. 12 is a line graph showing slit lamp examination scores over an 8 day period for the eyes shown in FIG. 11.
Figure 13:
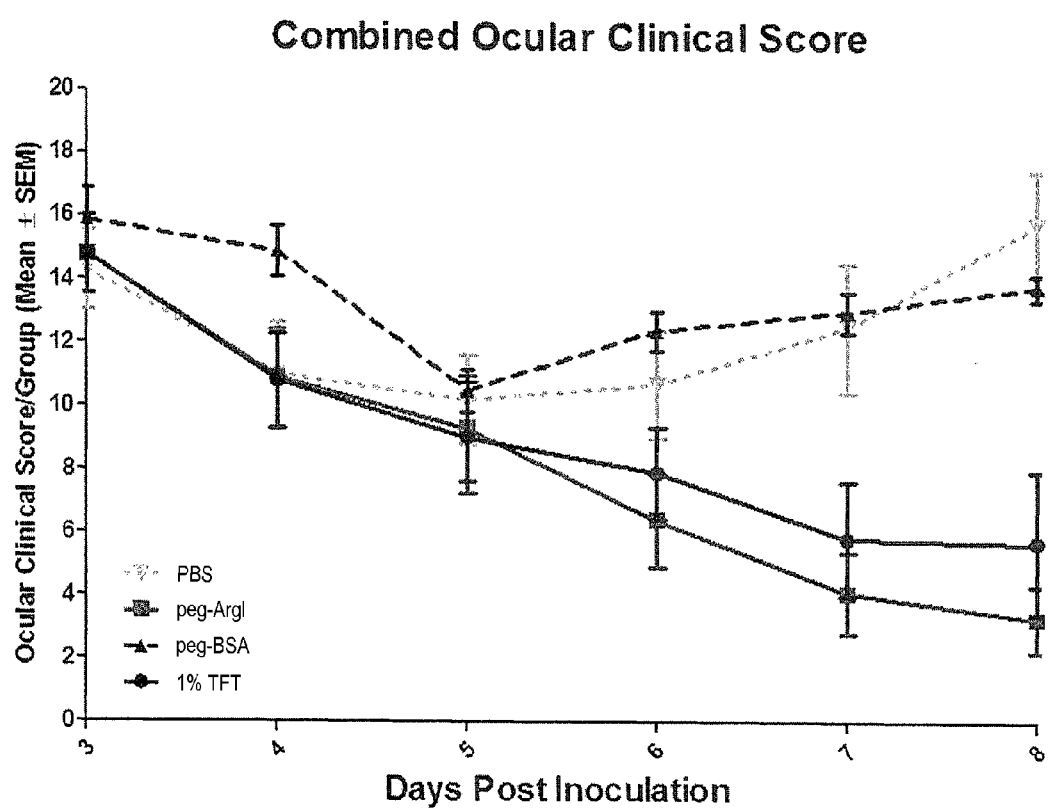
FIG. 13 is a line graph showing combined ocular clinical scores over an 8 day period for the eyes shown in FIG. 11.
Figure 14:
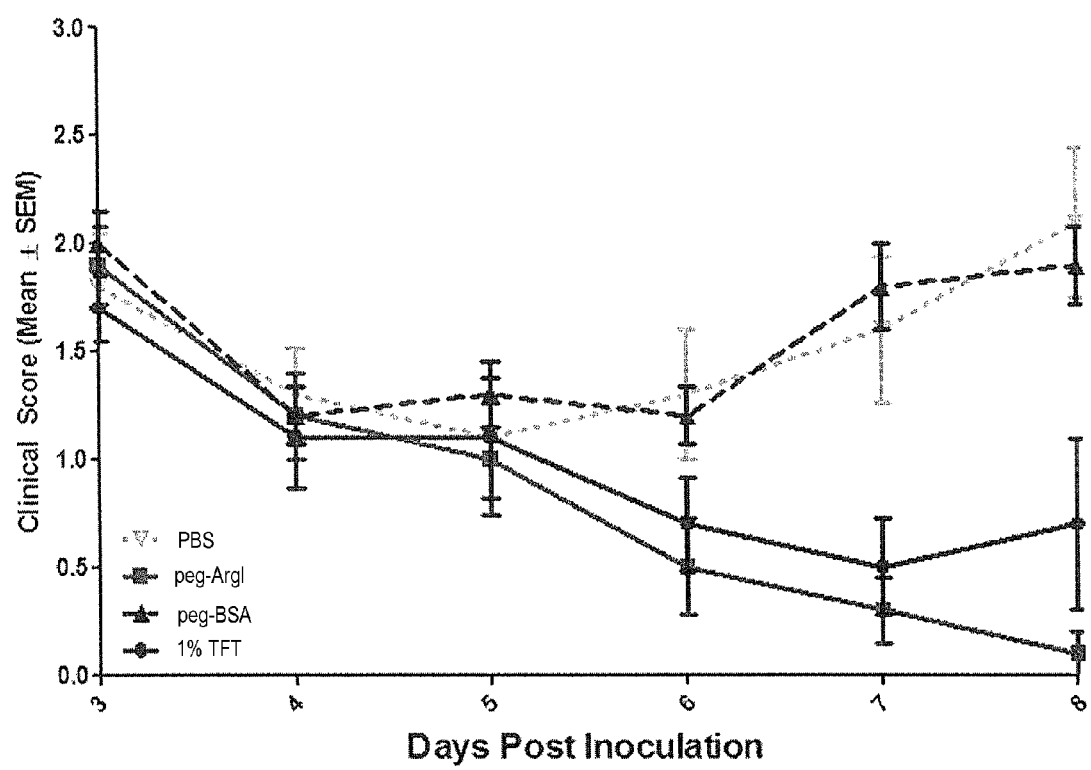
FIG. 14 is a line graph showing corneal stromal inflammation over an 8 day period for the eyes shown in FIG. 11.
Figure 15:
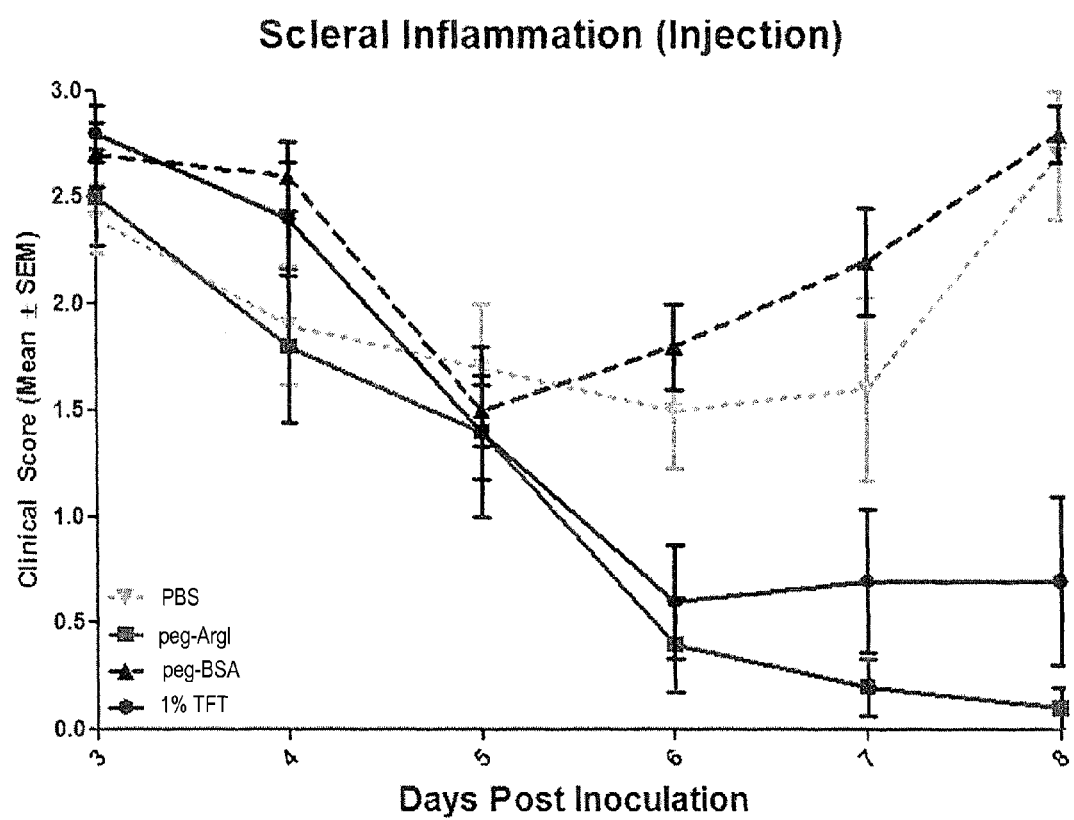
FIG. 15 is a line graph showing scleral inflammation over an 8 day period for the eyes shown in FIG. 11.
Figure 16:
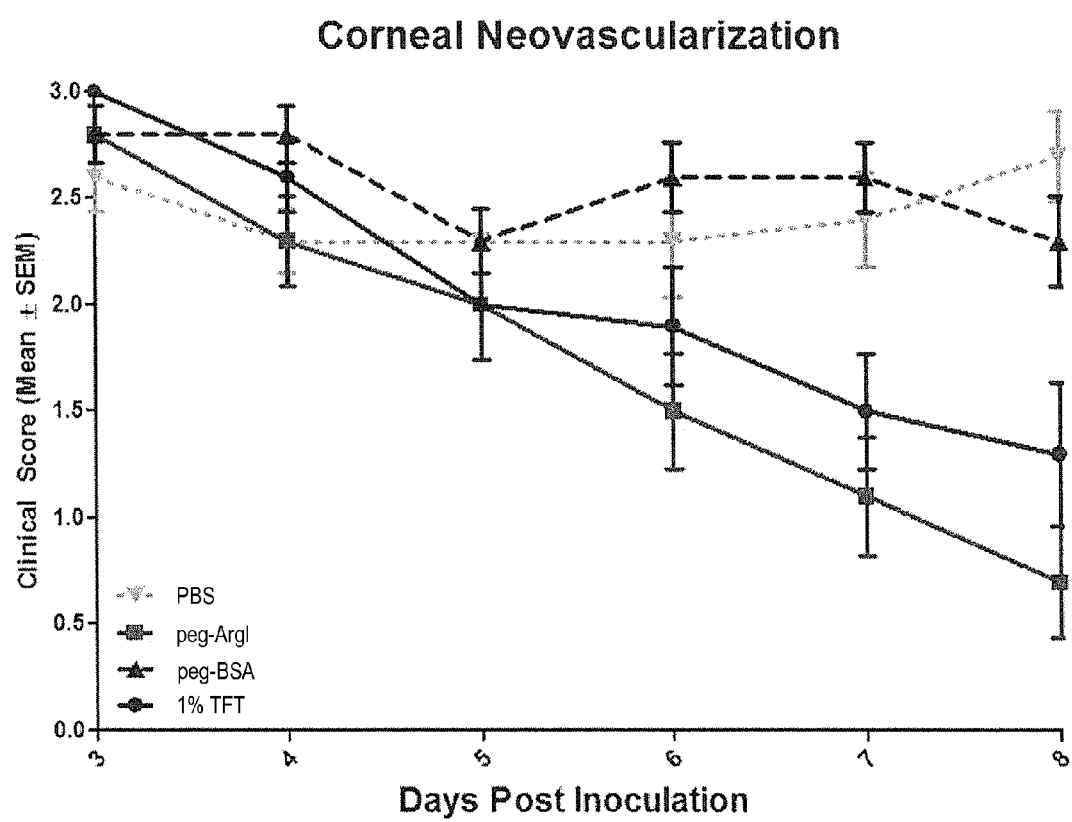
FIG. 16 is a line graph showing corneal neovascularization over an 8 day period for the eyes shown in FIG. 11.
Figure 17:
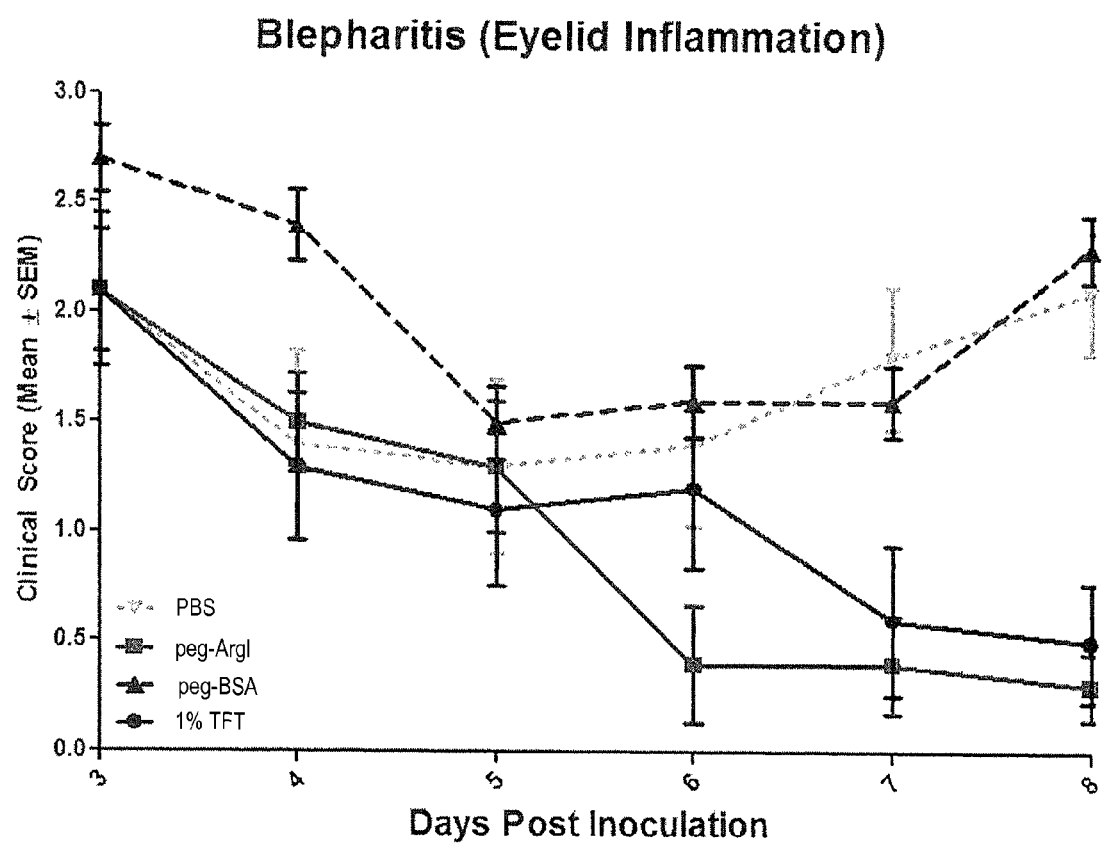
FIG. 17 is a line graph showing corneal eyelid inflammation over an 8 day period for the eyes shown in FIG. 11.

In an in vivo rabbit eye model system, the ability of peg-Arginase I to prevent HSV-mediated inflammation-associated disease was assessed relative to a commonly prescribed ophthalmic antiviral-1% triflourothymidine (TFT). Rabbit eyes were infected with HSV, and infection and disease were allowed to establish prior to beginning treatment. FIG. 10 illustrates that at day three post infection production of viral titers were matched, and that upon treatment with peg-Arginase I, infectious viral titers were barely detectable. These results were better than that observed for treatment with the anti-herpetic 1% TFT. FIG. 11 depicts representative overall clinical presentation of ocular herpetic disease. In either of the control (PBS or peg-BSA) treatment groups, severe blinding disease was observed following infection, with presence of severe inflammatory discharge and blinding epithelial defects observed by slit lamp examination. In contrast, both peg-Arginase I and 1% TFT showed marked reduction in the presence of dendritic or geographic ulceration, and improved clinical appearance. The statistical significance of these clinical scores comparing between treatment groups is shown in Table 6 and indicates that five days of treatment with peg-Arginase I statistically improved clinical presentation of disease and resolved many inflammation and neovascularization associated clinical parameters.

TABLE 6

Significance of Clinical Scores Between Treatment Groups (P values; P > 0.05 = NS)

| Group Comparison | Slit Lamp Examination | Combined Clinical | Corneal Neovasc. | Scleral Inflam. | Stromal Inflam. | Corneal Epithelium | Blephartis (Eyelid Infl.) |
| --- | --- | --- | --- | --- | --- | --- | --- |
| peg-ArgI vs peg-BSA | | | | | | | |

TABLE 6-continued

Significance of Clinical Scores Between Treatment Groups (P values; P > 0.05 = NS)

| Group Comparison | Slit Lamp Examination | Combined Clinical | Corneal Neovasc. | Scleral Inflam. | Stromal Inflam. | Corneal Epithelium | Blephartis (Eyelid Infl.) |
|---|---|---|---|---|---|---|---|
| Start of Tx | 1.0000 | 1.0000 | 1.0000 | 1.0000 | 1.0000 | 1.0000 | 0.9395 |
| DAY 7 peg-ArgI vs PBS | <0.0001 | 0.0032 | <0.0001 | <0.0001 | 0.0002 | 0.0003 | 0.0163 |
| Start of Tx | 1.0000 | 1.0000 | 1.0000 | 1.0000 | 1.0000 | 1.0000 | 1.0000 |
| DAY 7 1% TFT vs PEG-BSA | <0.0001 | 0.0088 | 0.0006 | 0.0049 | 0.0041 | 0.0426 | 0.0011 |
| Start of Tx | 1.0000 | 1.0000 | 1.0000 | 1.0000 | 1.0000 | 1.0000 | 0.9395 |
| DAY 7 1% TFT vs PBS | <0.0001 | NS | 0.0129 | 0.0012 | 0.0041 | 0.0125 | NS |
| Start of Tx | 1.0000 | 1.0000 | 0.9981 | 0.9999 | 1.0000 | 1.0000 | 1.0000 |
| DAY 7 | <0.0001 | NS | NS | NS | 0.0355 | NS | 0.0163 |

FIGS. 12 through 17 graphically depict assessment of the averages of these clinical parameters for each day throughout the duration of the experiment. Taken together, these results indicate that peg-Arginase I treatment not only prevents ocular replication of HSV, but can suppress and resolve virus-induced inflammation-associated disease and thwart vision-threatening vascularization of the cornea.

Figure 18:
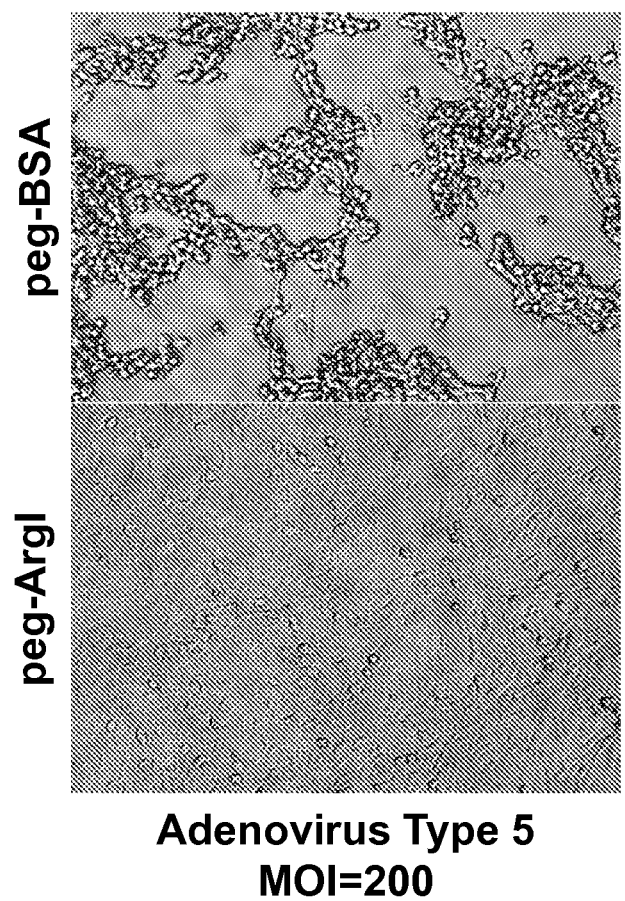
FIG. 18 is a pair of images of cell cultures infected with Adenovirus and treated with control (peg-BSA) or peg-Arginase I drops, according to an example embodiment of the present invention.

In another exemplary embodiment, the present disclosure may be employed to treat other inflammation-associated ocular diseases, such as those induced by Adenovirus infection. Clinical presentation following Adenoviral infection of the eye may proceed even when antiviral compounds, such as cidofovir, are present. Clinical presentation of Adenovirus-associated ocular disease may be due to uncontrolled inflammatory responses to the infection even following viral clearance. FIG. 18 illustrates that peg-Arginase I prevents Adenovirus-mediated cellular cytopathic effects and exhibits no toxicity to cells.

Figure 19:
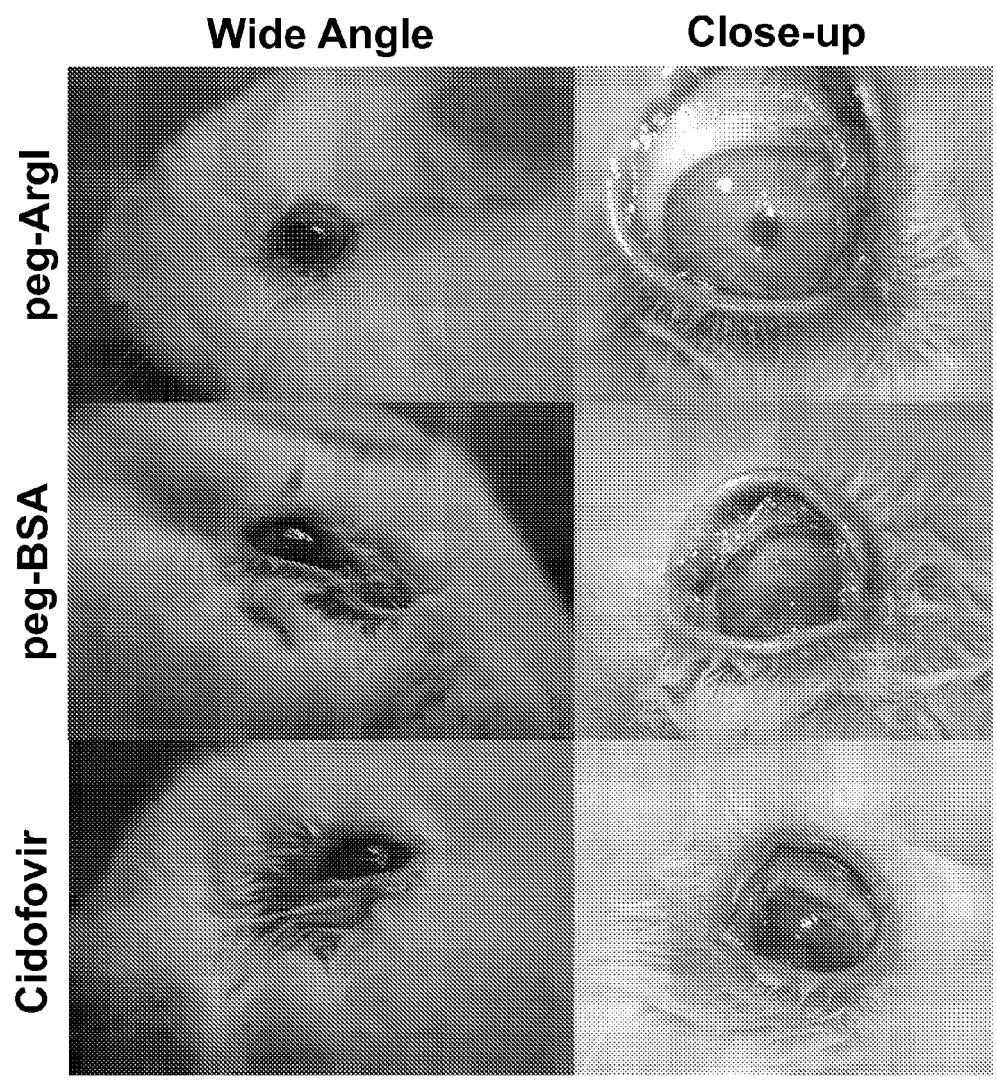
FIG. 19 is a series of images of rabbit eyes with an Adenoviral infection and treated with control (peg-BSA), cidofovir, or peg-Arginase I drops, according to an example embodiment of the present invention.
Figure 20:
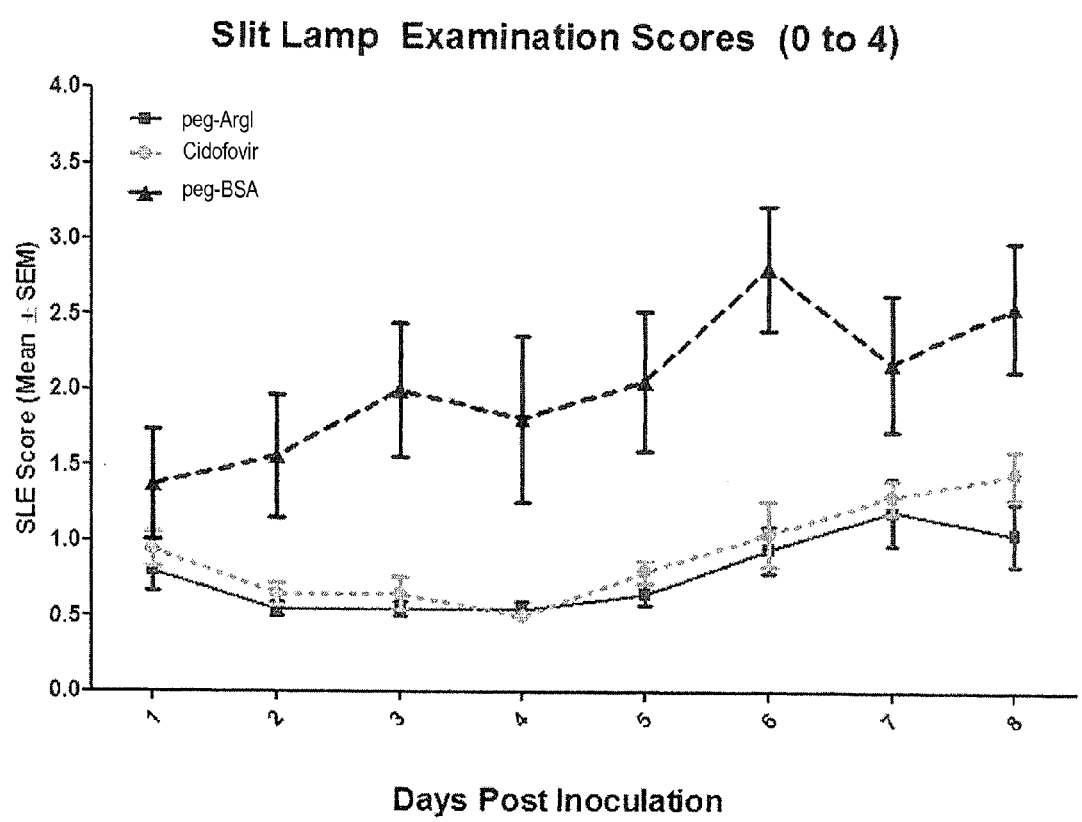
FIG. 20 is a line graph showing slit lamp examination scores over an 8 day period for the eyes shown in FIG. 19.
Figure 21:
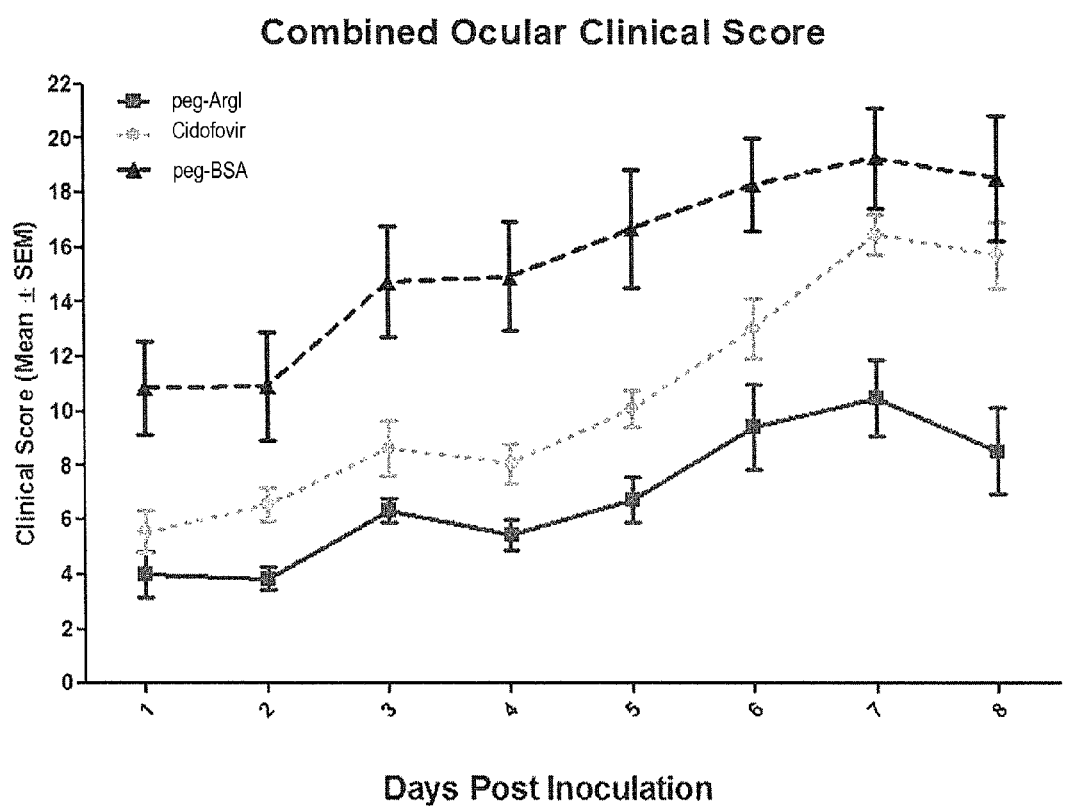
FIG. 21 is a line graph showing combined ocular clinical scores over an 8 day period for the eyes shown in FIG. 19.
Figure 22:
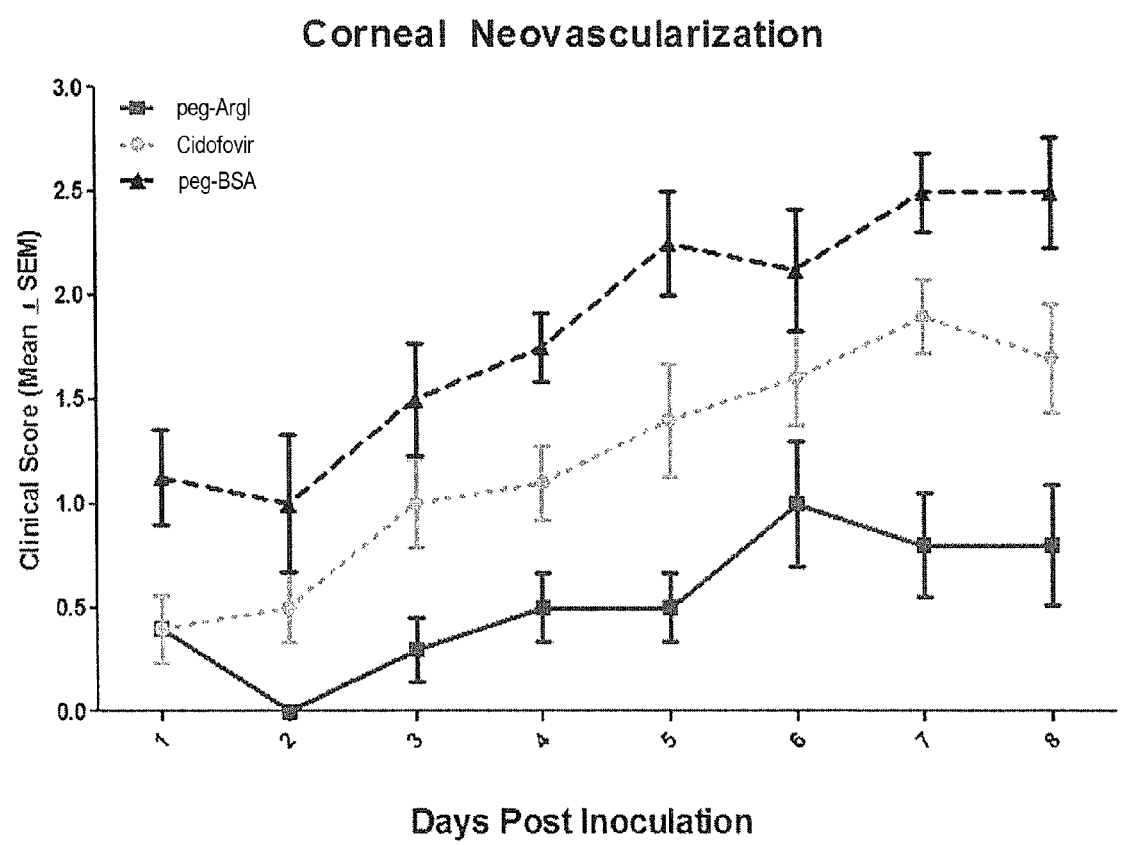
FIG. 22 is a line graph showing corneal neovascularization over an 8 day period for the eyes shown in FIG. 19.
Figure 23:
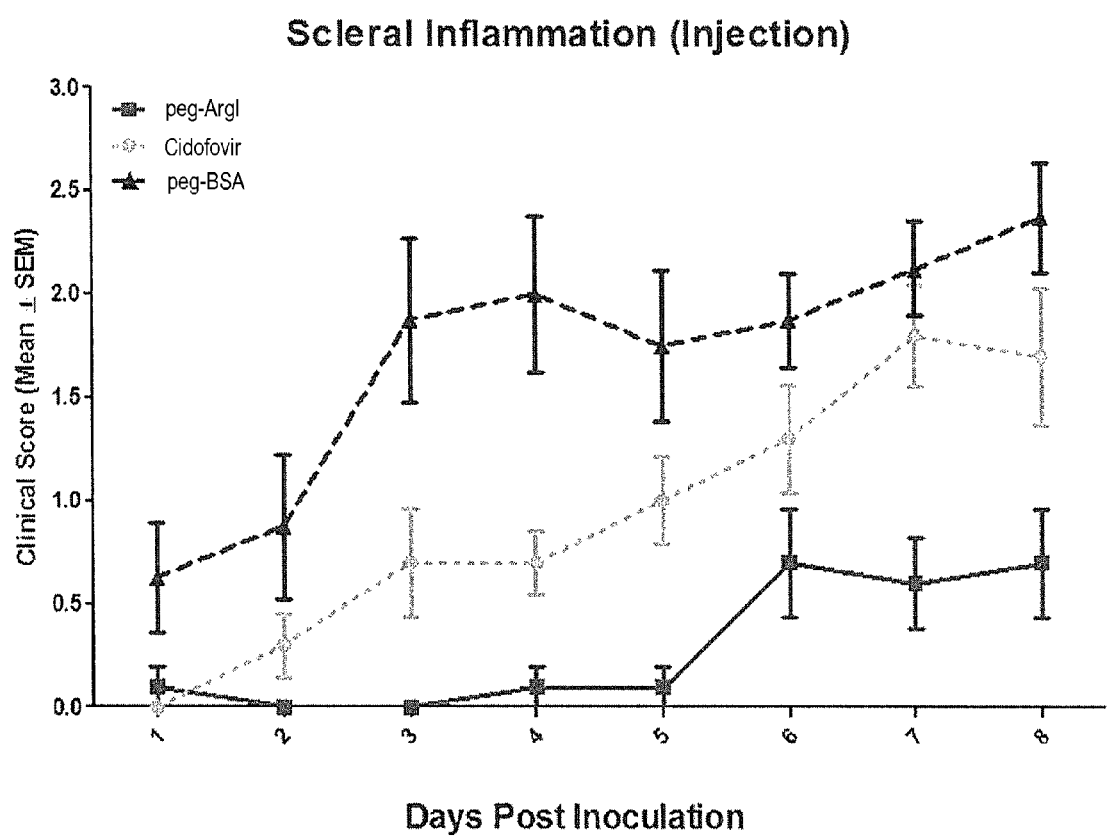
FIG. 23 is a line graph showing scleral inflammation over an 8 day period for the eyes shown in FIG. 19.
Figure 24:
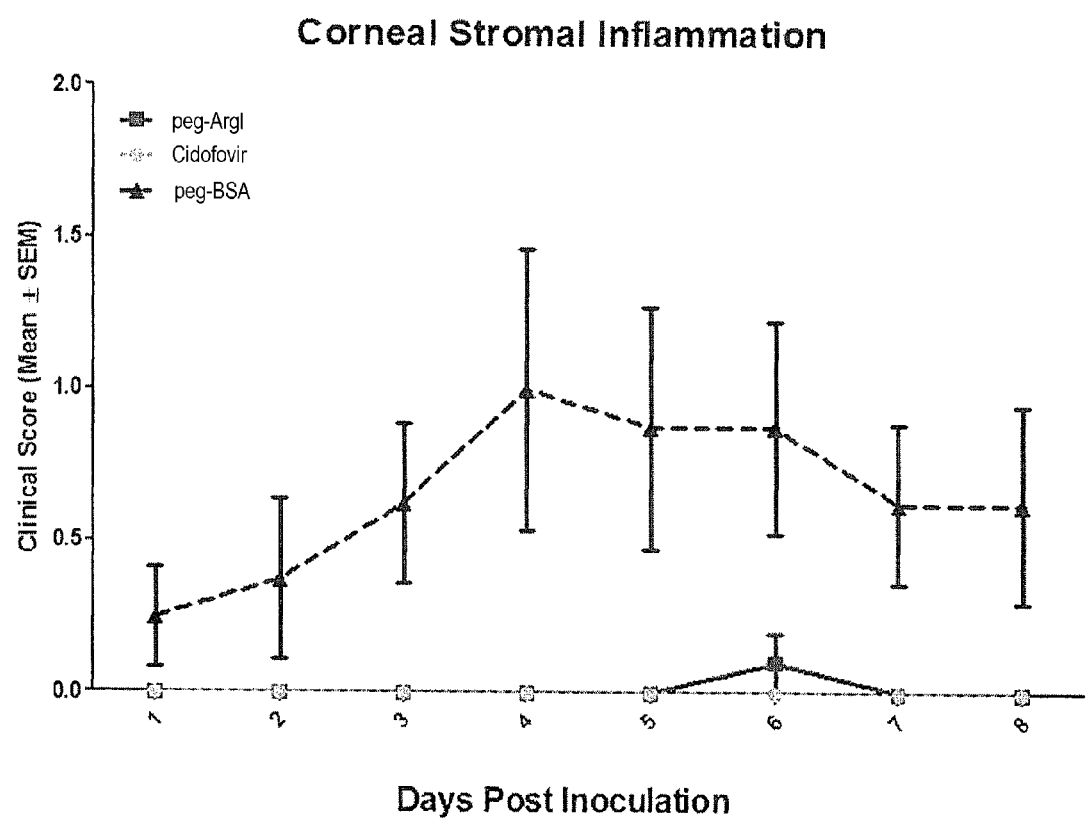
FIG. 24 is a line graph showing corneal stromal inflammation over an 8 day period for the eyes shown in FIG. 19.

In an in vivo rabbit eye model system, the ability of peg-Arginase I to prevent inflammation-associated disease following Adenoviral infection was examined. Rabbit eyes were infected with Adenovirus and eight hours later treatment was initiated. Eyes were treated four times daily with 10 U peg-Arginase I per 50 ul dose. FIG. 19 depicts representative images from the Adenovirus Type 5 "pink-eye" clinical disease rabbit eye model showing that peg-Arginase I treated eyes showed fewer clinical symptoms, including less corneal vascularization, epiphora, blepharitis, and scleral injection, compared to eyes treated with peg-BSA control or the potent antiviral cidofovir. FIGS. 20 through 24 illustrate that peg-Arginase I suppresses clinical presentation of disease at all treatment days, including suppression of ocular inflammation and neovascularization. These effects were independent of its ability to inhibit Adenoviral replication, since the antiviral cidofovir did not prevent clinical disease presentation. These properties of peg-Arginase I illustrate the present invention's utility in preventing numerous vision-threatening ocular diseases that present clinically as inflammation or neovascularization of the eye.

Figure 25A:
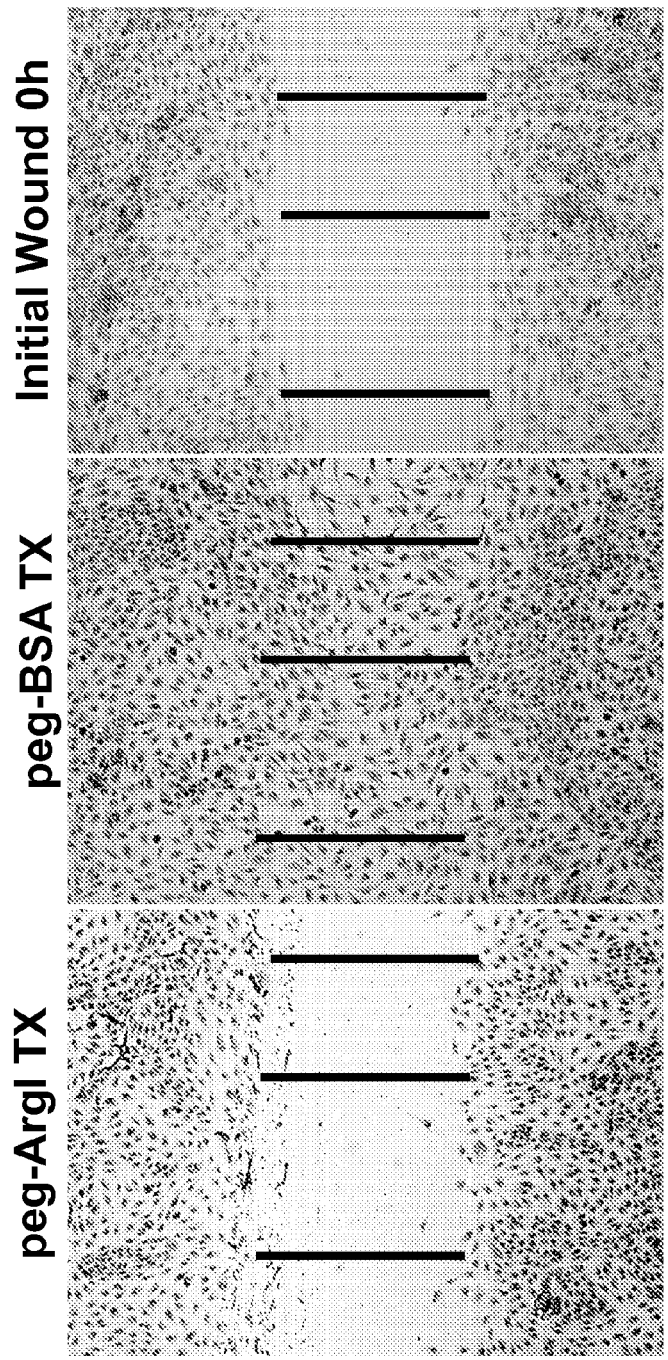
FIG. 25A is a series of images comparing effects of treatment with either control (peg-BSA) or peg-Arginase I on endothelial cell migration in a scratch wound healing model, according to an example embodiment of the present invention.
Figure 25B:
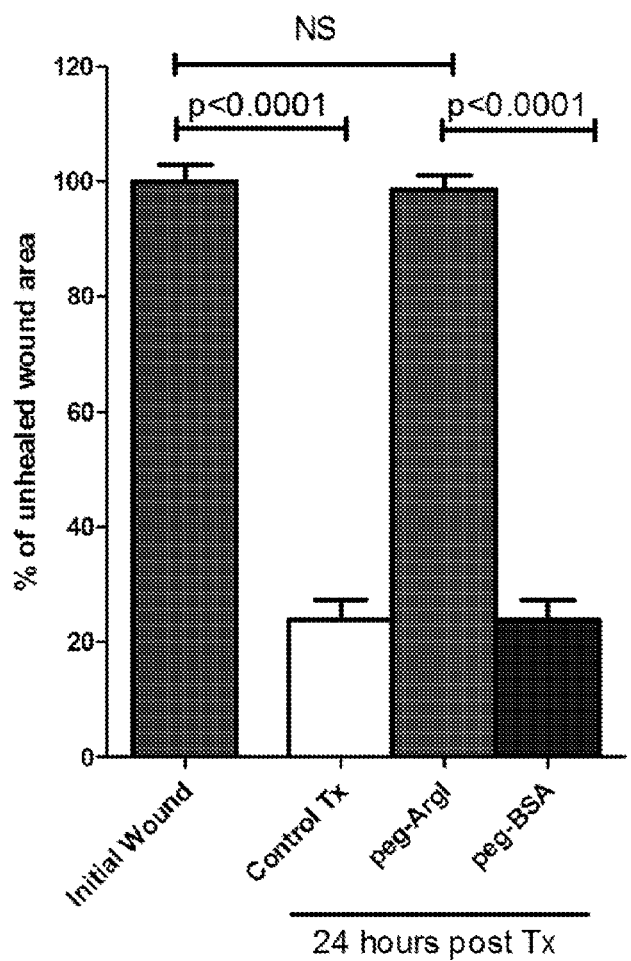
FIG. 25B is a bar graph showing a percentage of unhealed wound area after a twenty-four hour period for the wounds shown in FIG. 25A.

In another exemplary embodiment, the present disclosure may be employed to prevent and resolve corneal neovascularization and vascularization-associated edema. As observed in all other model systems, peg-Arginase I treatment prevented and/or reduced presentation of vascularization of the cornea, a vision-threatening condition that is associated with many ocular diseases. A key mediator and initiator of corneal vascularization may be vascular endothelial growth factor (VEGF). FIGS. 25A and 25B illustrate that peg-Arginase I prevents VEGF-mediated migration of primary vascular endothelial cells, a prerequisite for blood vessel growth and expansion onto the cornea.

Figure 26A:
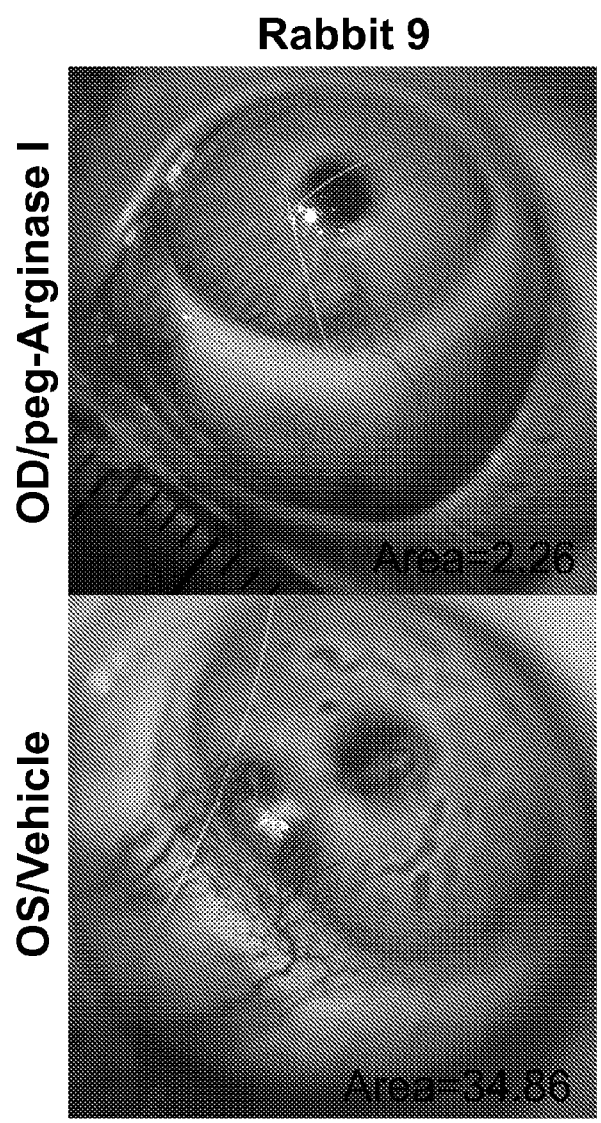
FIG. 26A is a pair of images of rabbit eyes having a VEGF pellet surgically implanted into a corneal micropocket and treated with vehicle or peg-Arginase I, according to an example embodiment of the present invention.
Figure 26B:
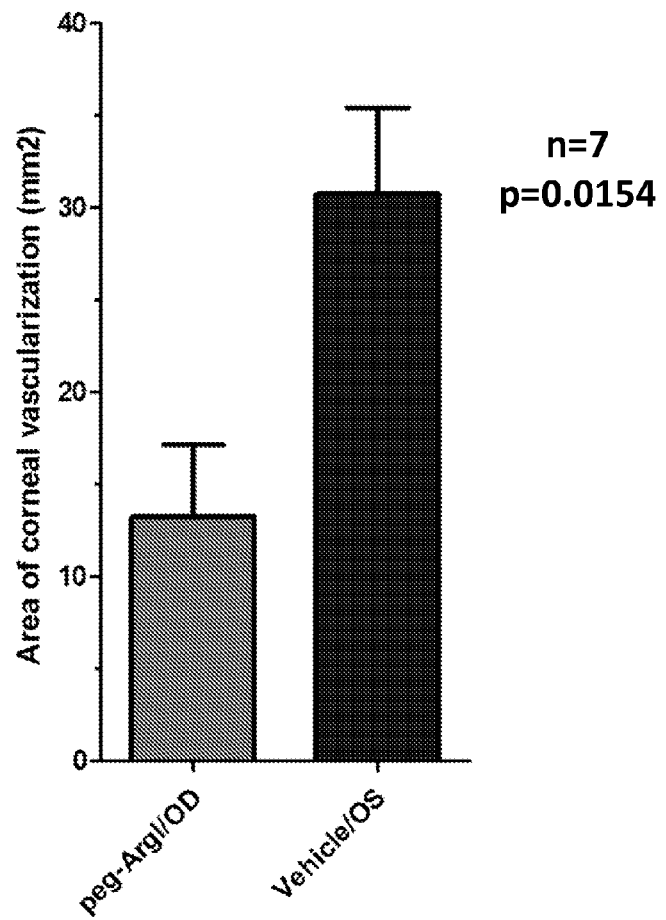
FIG. 26B is a bar graph showing areas of VEGF-mediated corneal neovascularization for the eyes shown in FIG. 26A.
Figure 27A:
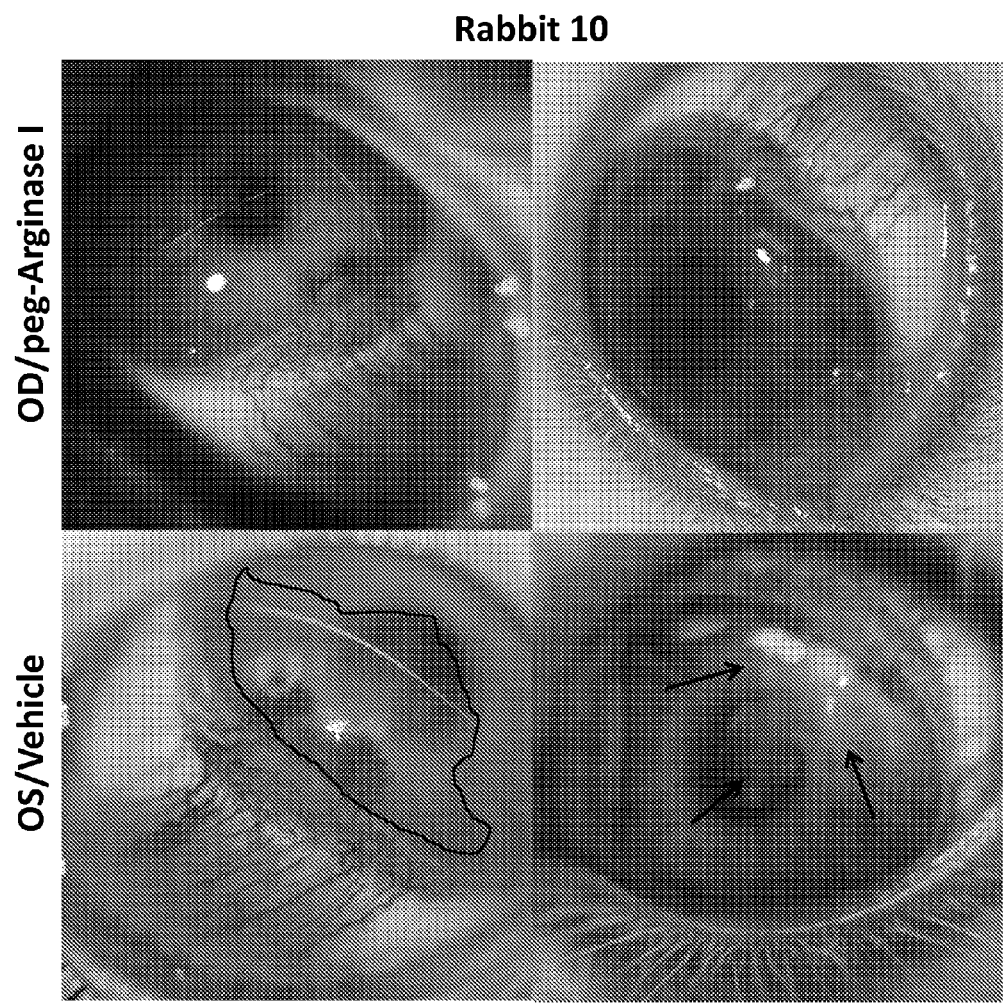
FIG. 27A is a series of images of a pair of rabbit eyes from the same rabbit showing clouding of the cornea in vehicle treated eyes, according to an example embodiment of the present invention.
Figure 27B:
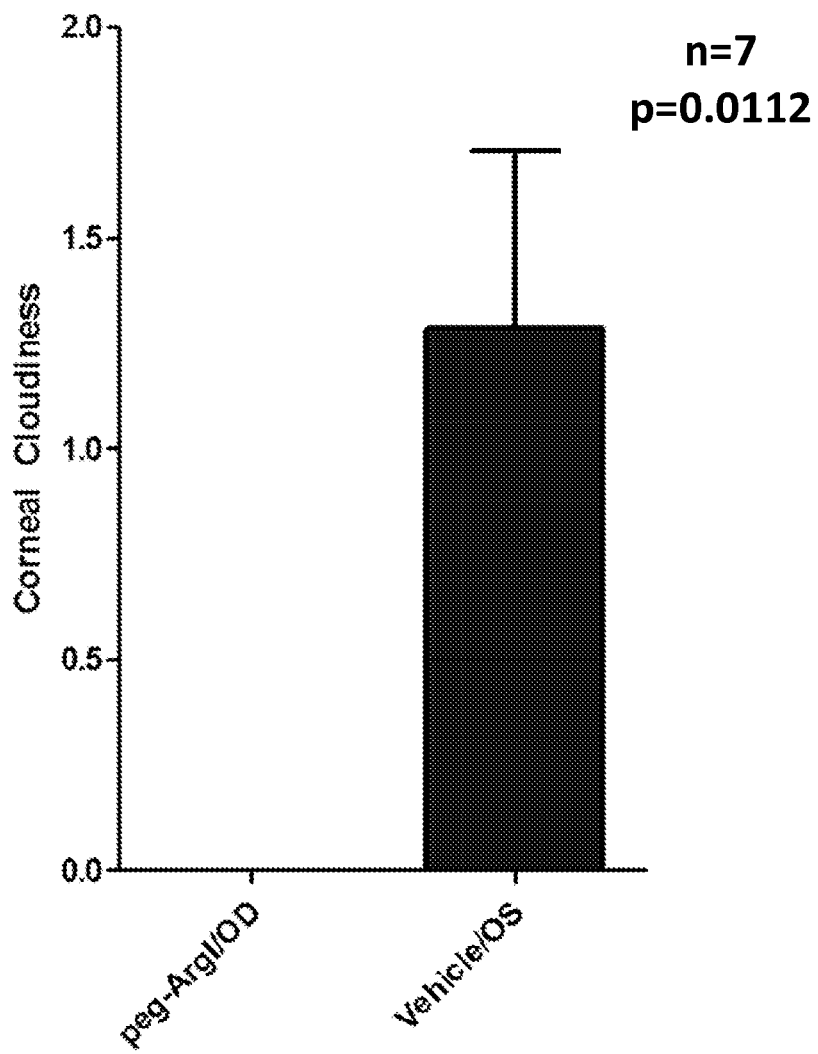
FIG. 27B is a bar graph showing corneal cloudiness measurements for the eyes shown in FIG. 27A.

In an in vivo rabbit eye model system, the ability of peg-Arginase I to prevent VEGF-mediated corneal vascularization was assessed by implanting slow release VEGF pellets within a corneal micropocket 3 mm from the corneal limbus. Eyes were subsequently treated with either peg-Arginase I (right, OD eye) or peg-BSA vehicle control (left, OS eye) 4 times daily at a dose of 10 U per 50 ul drop. FIGS. 26A and 26B demonstrate that the extent and areas of neovascularization of the cornea were significantly reduced in peg-Arginase I treated eyes compared to peg-BSA treated controls. Moreover, even when vascularization was present, FIGS. 27A and 27B establish that peg-Arginase I treatment prevented the appearance of corneal edema that resulted in corneal clouding and epithelial defects. As shown, peg-Arginase I inhibits vision-threatening corneal vascularization, further enabling peg-Arginase I to prevent and ameliorate vision-threatening aspects of many ocular diseases. Moreover, inhibition of vascularization assists in suppressing deleterious inflammatory responses.

While the embodiments are described with reference to various implementations and exploitations, it will be understood that these embodiments are illustrative and that the scope of the inventions is not limited to them. Many variations, modifications, additions, and improvements are possible. Further still, any steps described herein may be carried out in any desired order, and any desired steps may be added or deleted. The specification and drawings are accordingly to be regarded in an illustrative rather than in a restrictive sense.

What is claimed is:

1. A method, comprising the steps of:
   exogenously applying peg-Arginase I to an eye that has been infected by a drug resistant infectious agent;
   simultaneously inhibiting inflammation and neovascularization of corneal tissue of the eye; and
   promoting healing of the eye.
2. The method of claim 1, wherein the drug resistant infectious agent is a virus.

3. The method of claim 2, wherein the virus is one of HSV-1, HSV-2, CMV, VZV and Adenovirus.

4. The method of claim 2, wherein the peg-Arginase I inhibits replication of the virus.

5. The method of claim 1, wherein the drug resistant infectious agent is a bacteria.

6. The method of claim 5, wherein the bacteria is *Chlamydia trachomatis*.

7. The method of claim 1, wherein the peg-Arginase I is part of an ophthalmic formulation.

8. The method of claim 7, wherein the ophthalmic formulation comprises peg-Arginase I and free peg molecules.

9. The method of claim 8, wherein the ophthalmic formulation further comprises pH buffers.

10. The method of claim 7, wherein the ophthalmic formulation is an eye drop.

11. The method of claim 1, wherein the eye is a mammalian eye.

12. The method of claim 11, wherein the mammalian eye is a human eye.

13. A therapeutic method to treat an ocular disease, comprising: applying peg-Arginase I to an affected eye;
    wherein the peg-Arginase I is part of an ophthalmic formulation; and
    wherein the ocular disease is caused by an infection by a drug resistant infectious agent.

14. The therapeutic method of claim 13, wherein the affected eye presents with at least one of inflammation and neovascularization.

15. The therapeutic method of claim 13, wherein the drug resistant infectious agent is a virus.

16. The therapeutic method of claim 15, wherein the peg-Arginase I inhibits replication of the virus.

17. The method of claim 13, wherein the drug resistant infectious agent is a bacteria.

18. An ocular anti-viral treatment, comprising: applying peg-Arginase I to an infected eye;
    wherein the peg-Arginase I is part of an ophthalmic formulation; and
    wherein the infected eye has been infected by a drug resistant virus.

19. The treatment of claim 18, wherein replication of the drug resistant virus is inhibited.

20. The treatment of claim 18, wherein the drug resistant virus is at least one of HSV-1, HSV-2, CMV, VZV and Adenovirus.

21. A method to prevent ocular neovascularization, comprising:
    applying peg-Arginase I to an affected eye;
    wherein the peg-Arginase I is part of an ophthalmic formulation; and
    wherein the eye that has been infected by a drug resistant infectious agent.

22. The method of claim 21, wherein the ophthalmic formulation is comprised of peg-Arginase I and free peg molecules.

23. A method to prevent ocular inflammation, comprising:
    applying peg-Arginase I to an affected eye;
    wherein the peg-Arginase I is part of an ophthalmic formulation; and
    wherein the eye that has been infected by a drug resistant infectious agent.

24. The method of claim 23, wherein the ophthalmic formulation is comprised of peg-Arginase I and free peg molecules.

* * * * *

UNITED STATES PATENT AND TRADEMARK OFFICE
CERTIFICATE OF CORRECTION

Page 1 of 1

PATENT NO. : 8,877,183 B2
APPLICATION NO. : 13/828669
DATED : November 4, 2014
INVENTOR(S) : Timothy Paul Foster et al.

It is certified that error appears in the above-identified patent and that said Letters Patent is hereby corrected as shown below:

In the Specification

At Column 1, Line numbers 14-17, change:
"This invention was made with government support under grants P20RR021970 and P20GM103501 awarded by the National Institutes of Health. The government has certain rights in the invention."

To:
--This invention was made with government support under grants R01CA107974, R01AI112402, P20RR021970 and P20GM103501 awarded by the National Institutes of Health. The government has certain rights in the invention.--

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*